(12) United States Patent
Jerri et al.

(10) Patent No.: US 11,135,561 B2
(45) Date of Patent: Oct. 5, 2021

(54) MICROCAPSULES HAVING A MINERAL LAYER

(71) Applicant: FIRMENICH SA, Satigny (CH)

(72) Inventors: Huda Jerri, Plainsboro, NJ (US); Nicholas Impellizzeri, Plainsboro, NJ (US); Valery Normand, Plainsboro, NJ (US)

(73) Assignee: Firmenich SA, Satigny (CH)

( * ) Notice: Subject to any disclaimer, the term of this patent is extended or adjusted under 35 U.S.C. 154(b) by 85 days.

(21) Appl. No.: 16/471,804

(22) PCT Filed: Dec. 21, 2017

(86) PCT No.: PCT/EP2017/084178
§ 371 (c)(1),
(2) Date: Jun. 20, 2019

(87) PCT Pub. No.: WO2018/115330
PCT Pub. Date: Jun. 28, 2018

(65) Prior Publication Data
US 2020/0114328 A1    Apr. 16, 2020

Related U.S. Application Data

(60) Provisional application No. 62/438,155, filed on Dec. 22, 2016.

(30) Foreign Application Priority Data

Jan. 18, 2017    (EP) .................................... 17151928

(51) Int. Cl.
*B01J 13/16*    (2006.01)
*B01J 13/22*    (2006.01)
(Continued)

(52) U.S. Cl.
CPC ............... *B01J 13/16* (2013.01); *B01J 13/22* (2013.01); *B32B 5/16* (2013.01); *C11D 3/505* (2013.01)

(58) Field of Classification Search
CPC .. B01J 13/16; B01J 13/22; B32B 5/16; C11D 3/505; A61K 8/11; A61K 2800/56
(Continued)

(56) References Cited

U.S. PATENT DOCUMENTS

2006/0216509 A1    9/2006 Kleban et al.
2009/0256107 A1*  10/2009 Hentze ..................... B01J 13/14
                                                        252/73

(Continued)

FOREIGN PATENT DOCUMENTS

EP    2300146 B1    3/2017
EP    2579976 B1    8/2017
(Continued)

OTHER PUBLICATIONS

Chatterjee "The Influence of 1-Butanol and Trisodium Citrate Ion on Morphology and Chemical Properties of Chitosan-Based Microcapsules during Rigidification by Alkali Treatment." Mar. Drugs 2014, 12, 5801-5816. (Year: 2014).*

(Continued)

*Primary Examiner* — Tri V Nguyen
(74) *Attorney, Agent, or Firm* — Armstrong Teasdale LLPFi

(57) ABSTRACT

Described herein is a mineralized core-shell microcapsule slurry including at least one microcapsule having:
a) an oil-based core including a hydrophobic active ingredient;
b) a polymeric shell having a terminating charged functional surface; and
c) a mineral layer on the terminating charged functional surface.

(Continued)

Capsule A          Capsule B          Capsule C

Capsule X          Capsule Y          Capsule Z

Also described herein is a process for a preparation of said microcapsules. Also described herein are perfuming compositions and consumer products including said microcapsules, including perfumed consumer products in the form of home care or personal care products.

18 Claims, 9 Drawing Sheets

(51) Int. Cl.
*C11D 3/50* (2006.01)
*B32B 5/16* (2006.01)

(58) Field of Classification Search
USPC .............................. 428/402.2, 402.21, 403
See application file for complete search history.

(56) References Cited

U.S. PATENT DOCUMENTS

| | | | |
|---|---|---|---|
| 2011/0110993 A1* | 5/2011 | Chieffi | A61K 8/731 424/401 |
| 2015/0252312 A1* | 9/2015 | de Villeneuve | A23L 27/72 510/515 |
| 2016/0168511 A1 | 6/2016 | Hitchcock et al. | |
| 2018/0009996 A1 | 1/2018 | Lentz et al. | |
| 2018/0243717 A1* | 8/2018 | Macedo Tavares | B01J 13/16 |

FOREIGN PATENT DOCUMENTS

| | | | | |
|---|---|---|---|---|
| EP | 3318323 | A1 | 5/2018 | |
| WO | 0141915 | A1 | 6/2001 | |
| WO | 2007004166 | A1 | 1/2007 | |
| WO | 2009153695 | A1 | 12/2009 | |
| WO | 2010003762 | A1 | 1/2010 | |
| WO | WO-2010003762 | A1 * | 1/2010 | ........... A23K 20/179 |
| WO | 2013068255 | A1 | 5/2013 | |
| WO | 2013092375 | A1 | 6/2013 | |
| WO | 2015110568 | A1 | 7/2015 | |
| WO | 2016100477 | A1 | 6/2016 | |
| WO | 2016193435 | A1 | 12/2016 | |
| WO | 2018054719 | A1 | 3/2018 | |

OTHER PUBLICATIONS

Elabbadi et al., "Sustainable Delivery Systems: Retention of Model Volatile Oils Trapped on Hybrid Calcium Carbonate Microparticles", ACS Sustainable Chem. Eng., Published Jul. 27, 2015, vol. 3, No. 9, pp. 2178-2186.
S. Arctander, "Perfume and Flavor Chemicals", Molecules 2195-2201 and 2574-2575, Published 1969.
International Search Report for International Application No. PCT/EP2017/084178, dated Apr. 17, 2018, 4 pages.
European Search Report for EP Patent Application No. 17818582.3, dated Jul. 30, 2020, 7 pages.

* cited by examiner

MICROCAPSULES HAVING A MINERAL LAYER

CROSS-REFERENCE TO RELATED APPLICATIONS

This application is a U.S. National Phase Application of PCT/EP2017/084178, filed Dec. 21, 2017, which claims the benefit of priority to U.S. Provisional Application 62/438,155, filed Dec. 22, 2016, and the benefit of priority to European Patent Application No. 17151928.3, filed Jan. 18, 2017, the entire contents of which are hereby incorporated by reference herein.

TECHNICAL FIELD

The present invention relates to the field of delivery systems. More specifically, the present invention relates to microcapsules comprising a hydrophobic active ingredient-based core, preferably a perfume or a flavour, a polymeric shell and a mineral layer onto the polymeric shell. A process for the preparation of said microcapsules is also an object of the invention. Perfuming compositions and consumer products comprising said microcapsules, in particular perfumed consumer products in the form of fine fragrance, home care or personal care products, are also part of the invention.

BACKGROUND OF THE INVENTION

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

In order to be successfully used in consumer products, perfume delivery systems must meet a certain number of criteria. The first requirement concerns stability in aggressive medium. In fact delivery systems may suffer from stability problems, in particular when incorporated into surfactant-based products such as detergents, wherein said systems tend to degrade and lose efficiency in the perfume-retention ability. It is also difficult to have a good stability and a good dispersion of the capsules altogether. The dispersion factor is very important because the aggregation of capsules increases the tendency of the capsule-containing product to phase separate, which represents an real disadvantage. On the other hand, perfume delivery systems must also perform during the actual use of the end-product by the consumer, in particular in terms of odor performance, as the perfume needs to be released when required. Another issue faced for example by the perfumery industry is to provide delivery systems that are well deposited on the substrate for the treatment of which the end product is intended to be used, such as textile, skin, hair or other surfaces, so as to possibly remain on the substrate even after a rinsing step. To address this specific problem, the use of cationic capsules has been described in the prior art. Cationic capsules are also known to be better dispersed in several applications.

For example, WO 01/41915 discloses a process for the preparation of capsules carrying cationic charges. Such a process is allegedly applicable to a large variety of microcapsules, in particular polyurethane-polyurea microcapsules are mentioned. After their formation, the capsules are placed in a medium which is favourable for the treatment with cationic polymers. The treatment with cationic polymers is carried out after purification of the basic capsule slurry, in order to eliminate anionic or neutral polymers which were not incorporated in the capsule wall during formation thereof, and other free electrically charged compounds involved in the encapsulation process. In particular, the capsules are diluted, isolated and then re-suspended in water, or even washed to further eliminate anionic compounds. After the purification step, the capsules are agitated vigorously and the cationic polymers are added. Partially quaternized copolymers of polyvinylpyrrolidones are cited to this purpose, among many other suitable polymers. The described process comprises several steps following the capsule formation, said process being therefore time consuming and not economically profitable.

US 2006/0216509 also discloses a process to render polyurea capsules positively-charged. This process involves the addition, during the wall formation, of polyamines, the capsules thus bearing latent charges, depending on the pH of the medium. Once formed, the capsules are subsequently cationized by acid action or alkylation to bear permanent positive charges. The cationic compounds therefore react with the capsule wall, chemically changing the latter.

WO2009/153695 discloses a simplified process for the preparation of polyurea microcapsules bearing permanent positive charges based on the use of a specific stabilizer and which present good deposition on a substrate.

Despite those prior disclosures, there is still a need to improve the ability of hydrophobic active ingredient (for example perfume) delivery systems to deposit on a substrate and to adhere on the substrate for leave-on and rinse-off applications, while performing in terms of hydrophobic active ingredient release and stability.

The microcapsules of the invention solve this problem as they proved to show improvement in terms of deposition properties compared to what was known heretofore such as cationic delivery systems.

SUMMARY OF THE INVENTION

The present invention provides microcapsules with boosted deposition properties. In particular, the specific growth of a mineral layer onto a terminating charged surface of the microcapsule is unexpectedly tremendously improving the percentage of deposition of microcapsules on a substrate.

A first object of the invention is therefore a mineralized core-shell microcapsule slurry comprising at least one microcapsule having:
 a) an oil-based core comprising a hydrophobic active ingredient, preferably a perfume;
 b) a polymeric shell having a terminating charged functional surface; and
 c) a mineral layer on the terminating charged functional surface.

A second object of the invention is a process for preparing a mineralized core-shell microcapsule slurry as defined above comprising the steps of:
 (i) Preparing a microcapsule core-shell slurry comprising microcapsules having a terminating charged functional surface;
 (ii) Adsorption of at least one mineral precursor on the charged surface;
 (iii) Applying conditions suitable to induce crystal growth of the mineral on the charged surface to form a mineral layer.

A third object of the invention is a perfuming composition comprising the microcapsules as defined above, wherein the oil-based core comprises a perfume.

A fourth object of the invention is a consumer product comprising the microcapsules or a perfuming composition as defined above.

A fifth object of the invention is a method for improving deposition of microcapsules on a surface, which comprises treating said surface with a perfuming composition or a consumer product as defined above.

DETAILED DESCRIPTION OF THE INVENTION

Figure 1:
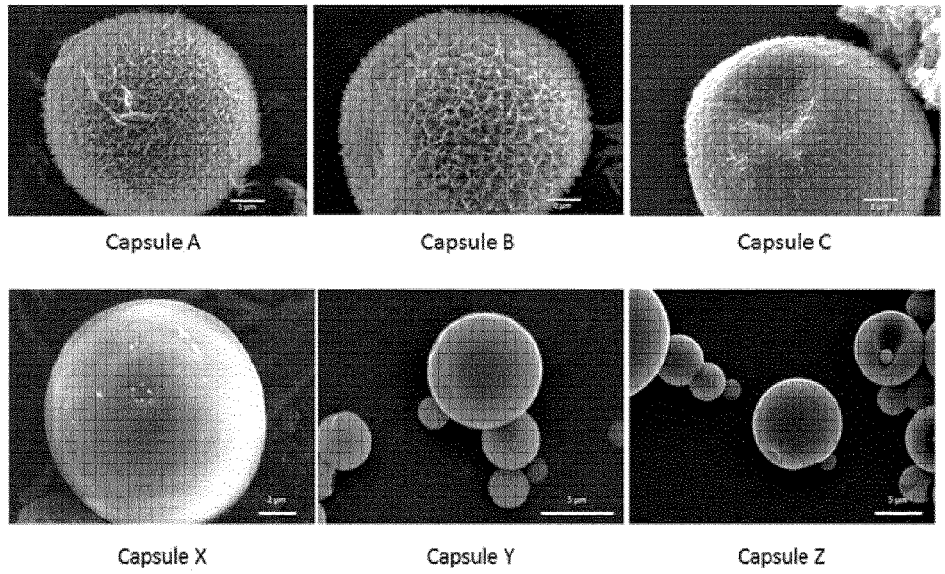
FIG. 1 represents scanning electron micrographs of mineralized microcapsules according to the invention (Capsules A, B, and C) compared to smooth, unmineralized control capsules (Capsules X, Y, and Z).

Unless stated otherwise, percentages (%) are meant to designate a percentage by weight of a composition.

Definitions

A "core-shell microcapsule", or the similar, in the present invention is meant to designate a capsule that has a particle size distribution in the micron range (e.g. a mean diameter (d(v, 0.5)) comprised between about 1 and 3000 μm) and comprises an external solid oligomer-based shell or a polymeric shell and an internal continuous phase enclosed by the external shell. For avoidance of doubts coacervates are considered as core-shell microcapsules in the present invention.

By "mineralized core-shell microcapsule", it should be understood a microcapsule having a mineralized surface induced by growth of inorganic solid crystalline material.

By "charged emulsifier" it should be understood a compound having emulsifying properties and that is negatively charged and/or positively charged. The charged emulsifier can be a charged biopolymer.

By "charged biopolymer" it should be understood a biopolymer that is negatively charged (anionic biopolymer), and/or positively charged (cationic or protonated biopolymer), and/or zwitterionic. As non-limiting examples, one may cite gum acacia, pectin, sericin, sodium caseinate and amphiphilic proteins such as soy, pea, milk, bovine serum albumin, gelatin as anionic biopolymers.

By "biopolymers" it is meant biomacromolecules produced by living organisms. Biopolymers are characterized by molecular weight distributions ranging from 1,000 (1 thousand) to 1,000,000,000 (1 billion) Daltons. These macromolecules may be carbohydrates (sugar based) or proteins (amino-acid based) or a combination of both (gums) and can be linear or branched. The biopolymers according to the invention may be further chemically modified.

According to an embodiment, biopolymers are amphiphilic or anionic namely negatively charged in water at a pH greater than 9.

In the context of the invention, a "mineral layer" is composed of a stable inorganic crystalline phase that grows normal to the terminating charged surface of the shell to yield a rough, spinulose, rugose, platy, ridged or otherwise highly textured mineral aspect.

By "mineral precursor", it should be understood a mineral precursor required for growth of the desired crystalline phase. The mineral precursor is preferably a mineral water-soluble salt containing the necessary ions for growth of the desired crystalline phase.

The terminology of "incubating" is used in the context of the present invention to describe the act of submerging the microcapsules in the precursor solution and allowing it time to interact with the microcapsules.

By "polyurea-based" wall or shell, it is meant that the polymer comprises urea linkages produced by either an amino-functional crosslinker or hydrolysis of isocyanate groups to produce amino groups capable of further reacting with isocyanate groups during interfacial polymerization.

By "polyurethane-based" wall or shell, it is meant that the polymer comprises urethane linkages produced by reaction of a polyol with the isocyanate groups during interfacial polymerization.

For the sake of clarity, by the expression "dispersion" in the present invention it is meant a system in which particles are dispersed in a continuous phase of a different composition and it specifically includes a suspension or an emulsion.

By "hydrophobic active ingredient", it is meant any active ingredient—single ingredient or a mixture of ingredients—which forms a two-phase dispersion when mixed with water.

Hydrophobic active ingredients are preferably chosen from the group consisting of flavor, flavor ingredients, perfume, perfume ingredients, nutraceuticals, cosmetics, insect control agents, biocide actives and mixtures thereof.

The nature and type of the insect control agents present in the hydrophobic internal phase do not warrant a more detailed description here, which in any case would not be exhaustive, the skilled person being able to select them on the basis of its general knowledge and according to the intended use or application.

Examples of such insect control agents are birch, DEET (N,N-diethyl-m-toluamide), essential oil of the lemon eucalyptus (*Corymbia citriodora*) and its active compound p-menthane-3,8-diol (PMD), icaridin (hydroxyethyl isobutyl piperidine carboxylate), Nepelactone, Citronella oil, Neem oil, Bog Myrtle (Myrica Gale), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

According to a particular embodiment, the hydrophobic active ingredient consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odor. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodor counteraction, antimicrobial effect, microbial stability, insect control.

The nature and type of the perfuming ingredients present in the hydrophobic internal phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Core-Shell Microcapsule Slurry

A first object of the invention is therefore a mineralized core-shell microcapsule slurry comprising at least one microcapsule having:

a) an oil-based core comprising a hydrophobic active ingredient, preferably a perfume;

b) a polymeric shell having a terminating charged functional surface; and c) a mineral layer on the terminating charged functional surface.

According to the invention, it should be understood that the mineral layer forms a spinulose surface covered by small spikes, ridges or platy protuberances perpendicular to the terminating charged functional surface (typically having a length between 100 and 600 nm and having an aspect ratio greater than 1).

Indeed, the surface of the mineral layer has a rough, spiny, spiky, ridged, rugose, dendritic or textured appearance with rough heterogeneous crystalline features over the surface.

According to a particular embodiment, the mineral layer has an arithmetical mean roughness value ($R_a$) greater than 15 nm, preferably greater than 50 nm and/or a mean roughness depth ($R_z$) greater than 50 nm, preferably greater than 100 nm.

The instrument used in the present invention to evaluate surface features and determine surface roughness parameters $R_a$ and $R_z$ is a Keyence VK-X series confocal laser scanning microscope profilometer with a violet range laser.

A Dimension ICON Atomic Force Microscope (AFM) from Bruker was also used to evaluate the surface features.

Roughness parameters are well known by the skilled person in the art and can be defined as follows.

The arithmetical mean roughness value ($R_a$) is the average deviation of the surface height from the mean height of the roughness profile. The mean roughness depth ($R_z$) is the mean localized maximum roughness, or average peak-to-valley height difference per unit length analyzed.

A very good deposition is achieved with the microcapsules of the invention due notably to this specific spinulose or rough textured surface that adheres strongly to the targeted substrates.

Nature/Formation of the Shell

According to an embodiment, the polymeric shell is formed by interfacial polymerisation in the presence of a charged emulsifier.

One of the essential features of the present invention is that the polymeric shell has a terminating charged functional surface covered by a mineral layer. Different ways can be used to impart such charged surface on the polymeric shell. The terminating charged functional surface can be anionic or cationic.

According to a particular embodiment, the terminating charged functional surface is a terminating anionic functional surface.

Emulsifier=Anionic Emulsifier

According to a first embodiment, the charged emulsifier is an anionic emulsifier and forms an anionic surface once the interfacial polymerization is completed.

The anionic emulsifier can be amphiphilic materials, colloidal stabilizers or biopolymers.

According to an embodiment, the anionic emulsifier is selected from the group consisting of polyvinyl alcohol, polyvinyl pyrrolidone, gum acacia, casein, sodium caseinate, soy protein, pea protein, milk protein, whey protein, pectin, sericin, bovine serum albumin, gelatin, and mixtures thereof.

According to an embodiment, gum acacia is preferred.

According to a particular embodiment, the anionic surface (formed by the anionic emulsifier) is the terminating anionic functional surface that is directly covered by the mineral layer.

However, to improve the bonding of the mineral layer on the anionic surface, a polyelectrolyte scaffolding composed of oppositely-charge polyelectrolyte layer can be disposed between the anionic surface and the mineral layer.

Thus, according to a particular embodiment, the microcapsule comprises a polyelectrolyte scaffolding on the anionic surface, said polyelectrolyte scaffolding including at least one cationic polyelectrolyte layer and at least one anionic polyelectrolyte layer, the terminating layer being an anionic polyelectrolyte layer to form the terminating anionic functional surface of the shell.

According to this embodiment, the first layer of the polyelectrolyte scaffolding is a cationic polyelectrolyte layer disposed on the anionic surface (formed by the anionic emulsifier) and the last layer of the polyelectrolyte scaffolding is an anionic polyelectrolyte layer to form the terminating anionic functional surface on which the mineral layer is coated.

The number of layers of the polyelectrolyte scaffolding is not particularly limited.

According to a particular embodiment, the polyelectrolyte scaffolding consists of two pairs of oppositely charged polyelectrolytes layers.

It means that according to this embodiment, the microcapsule according to the invention comprises the following successive layers on the polymeric shell: a first cationic polyelectrolyte layer on the anionic surface (formed by the anionic emulsifier), a first negative polyelectrolyte layer, a second cationic polyelectrolyte layer, a second negative polyelectrolyte layer (forming the terminating anionic functional surface) and a mineral layer.

Emulsifier=Cationic Emulsifier

According to a second embodiment,
  the charged emulsifier is a cationic emulsifier that forms a cationic surface, and
  the microcapsule comprises at least one anionic polyelectrolyte layer on the cationic surface.

According to an embodiment, the cationic emulsifier is obtained by mixing a weakly anionic emulsifier (such as PVOH) with a strongly charged cationic polymer or polyquaternium (such as Salcare® SC-60 by BASF).

As non-limiting examples of cationic emulsifiers, one may cite for example cationic functionalized polyvinyl alcohol (as an example, cationic C-506 by Kuraray) or chitosan at an appropriate pH (typically at a weakly acidic pH (approximately pH 6.5).

According to a particular embodiment, the anionic surface (formed by the anionic polyelectrolyte layer) is the terminating anionic functional surface that is directly covered by the mineral layer.

According to another embodiment, at least one cationic polyelectrolyte layer and at least a second anionic polyelectrolyte layer are deposited successively on the anionic polyelectrolyte layer.

However, this embodiment is not limited to only one pair of opposite polyelectrolyte layers but includes 2, 3, 4 or even more of pair of opposite polyelectrolyte layers, with the proviso that the last polyelectrolyte layer is an anionic polyelectrolyte layer to form the terminating anionic functional surface.

According to an embodiment, the cationic polyelectrolyte layer is chosen in the group consisting of poly(allylamine hydrochloride), poly-L-lysine and chitosan.

According to another embodiment, the anionic polyelectrolyte layer is chosen in the group consisting of poly (sodium 4 styrene sulfonate) (PSS), polyacrylic acid, polyethylene imine, humic acid, carrageenan, gum acacia, and mixtures thereof.

According to a particular embodiment, the anionic polyelectrolyte layer is PSS.

The nature of the polymeric shell of the microcapsules of the invention can vary. As non-limiting examples, the shell can be made of a polymeric material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/gum acacia shell wall, coacervates and mixtures thereof.

Mineral Layer

According to the invention, the microcapsule comprises a mineral layer on the terminating charged functional surface. According to an embodiment, the terminating functional surface is anionic and can be obtained by using an anionic emulsifier with optionally a polyelectrolyte scaffolding as defined above or by using a cationic emulsifier with at least one anionic polyelectrolyte layer.

According to an embodiment, the mineral layer comprises a material chosen in the group consisting of iron oxides, iron oxyhydroxide, titanium oxides, zinc oxides, calcium carbonates, calcium phosphates and mixtures thereof. Preferably, the mineral layer is an iron oxide, an iron oxyhydroxide, or a calcium phosphate.

According to a particular embodiment, the mineral layer is iron oxyhydroxide goethite ($\alpha$-FeO(OH)).

According to another embodiment, the mineral layer is calcium phosphate.

According to a particular embodiment, the mineral layer does not comprise silicon oxides.

Another object of the invention is a core-shell microcapsule powder obtained by drying the core-shell microcapsule slurry as defined above.

Process for the Preparation of the Mineralized Core-Shell Microcapsule Slurry

Another object of the present invention is a process for preparing a mineralized core-shell microcapsule slurry as defined above comprising the steps of:
(i) Preparing a microcapsule core-shell slurry comprising microcapsules having a terminating charged functional surface;
(ii) Adsorption of at least one mineral precursor on the charged surface;
(iii) Applying conditions suitable to induce crystal growth of the mineral on the charged surface to form a mineral layer.

Step(i) Preparing a Core-Shell Microcapsule Slurry Comprising Microcapsules having a Terminating Charged Functional Surface According to an embodiment, the polymeric shell is formed by interfacial polymerisation in the presence of a charged emulsifier.

One of the essential features of the present invention is that the polymeric shell has a terminating charged functional surface on which a mineral precursor will be adsorbed in step (ii). Different ways can be used to impart such charged surface on the polymeric shell.

According to a particular embodiment, the terminating charged functional surface is a terminating anionic functional surface.

Emulsifier=Anionic Emulsifier

According to a first embodiment, the charged emulsifier is an anionic emulsifier and forms an anionic surface once the interfacial polymerization is completed.

The anionic emulsifier can be amphiphilic materials, colloidal stabilizers or biopolymers.

According to an embodiment, the anionic emulsifier is selected from the group consisting of polyvinyl alcohol, polyvinyl pyrrolidone, gum acacia, casein, sodium caseinate, soy (protein), hydrolyzed soy protein, pea protein, milk protein, whey protein, pectin, sugar beet pectin, sericin, bovine serum albumin, gelatin, and mixtures thereof.

According to an embodiment, gum acacia is preferred.

According to a particular embodiment, the anionic surface (formed by the anionic emulsifier) is the terminating anionic functional surface on which a mineral precursor will be adsorbed in step (ii).

However, to improve the bonding of mineral precursor on the anionic surface, step (i) can further comprise an additional step consisting of adding a polyelectrolyte scaffolding composed of oppositely-charge polyelectrolyte layer once the microcapsules are formed.

Thus, according to a particular embodiment, the polyelectrolyte scaffolding including at least one cationic polyelectrolyte layer and at least one anionic polyelectrolyte layer, the terminating layer being an anionic polyelectrolyte layer to form the terminating anionic functional surface of the shell.

According to this embodiment, the first layer of the polyelectrolyte scaffolding is a cationic polyelectrolyte layer disposed on the anionic surface (formed by the anionic emulsifier) and the last layer of the polyelectrolyte scaffolding is an anionic polyelectrolyte layer to form the terminating anionic functional surface on which on which a mineral precursor will be adsorbed in step (ii).

The number of layers of the polyelectrolyte scaffolding is not particularly limited.

According to a particular embodiment, the polyelectrolyte scaffolding consists of two pairs of oppositely charged polyelectrolytes layers.

It means that according to this embodiment, at the end of step (i), the microcapsule according to the invention comprises the following successive layers on the polymeric shell: a first cationic polyelectrolyte layer on the anionic surface (formed by the anionic emulsifier), a first negative polyelectrolyte layer, a second cationic polyelectrolyte layer, a second negative polyelectrolyte layer (forming the terminating anionic functional surface).

Emulsifier=Cationic Emulsifier

According to a second embodiment, the charged emulsifier is a cationic emulsifier that forms a cationic surface when the interfacial polymerization is completed, and wherein step (i) further comprises a step of coating at least one anionic polyelectrolyte layer on the cationic surface to form core-shell microcapsule having a terminating anionic functional surface. According to an embodiment, the cationic emulsifier is obtained by mixing a weakly anionic emulsifier (such as PVOH) with a strongly charged cationic polymer or polyquaternium (such as Salcare® SC-60 by BASF).

As non-limiting examples of cationic emulsifiers, one may cite for example cationic functionalized polyvinyl alcohol (as an example, cationic C-506 by Kuraray) or chitosan at an appropriate pH (typically at a weakly acidic pH (approximately pH 6.5).

According to a particular embodiment, the anionic surface (formed by the anionic polyelectrolyte layer) is the terminating anionic functional surface on which a mineral precursor will be adsorbed in step (ii).

According to another embodiment, at least one cationic polyelectrolyte layer and at least a second anionic polyelectrolyte layer are deposited successively on the anionic polyelectrolyte layer.

However, this embodiment is not limited to only one pair of opposite polyelectrolyte layers but includes 2, 3, 4 or even more of pair of opposite polyelectrolyte layers, with the proviso that the last polyelectrolyte layer is an anionic polyelectrolyte layer to form the terminating anionic functional surface.

According to an embodiment, the cationic polyelectrolyte layer is chosen in the group consisting of poly(allylamine hydrochloride), poly-L-lysine and chitosan.

According to another embodiment, the anionic polyelectrolyte layer is chosen in the group consisting of poly (sodium 4 styrene sulfonate) (PSS), polyacrylic acid, polyethylene imine, humic acid, carrageenan, gum acacia, and mixtures thereof.

According to a particular embodiment, the anionic polyelectrolyte layer is PSS.

The preparation of an aqueous slurry of core-shell microcapsules is well known from a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to an embodiment, capsules according to the present invention are polyurea-based capsules. According to a particular embodiment, interfacial polymerization is induced by addition of a polyamine reactant. Preferably, the reactant is selected from the group consisting of water soluble guanidine salts and guanazole to form a polyurea wall with the polyisocyanate. According to another embodiment, polyurea-based capsules are formed in absence of added polyamine reactant, and result only from the autopolymerization of the at least one polyisocyanate.

According to an embodiment, capsules according to the present invention are polyurethane-based capsules. According to this particular embodiment, interfacial polymerization is induced by addition of a polyol reactant. Preferably the reactant is selected from the group consisting of monomeric and polymeric polyols with multiple hydroxyl groups available for reaction and mixtures thereof.

According to another embodiment, capsules according to the present invention are polyurea/polyurethane based. In that case interfacial polymerization is induced by addition of a mixture of the reactant mentioned under precedent first and second embodiments.

Additionally, crosslinkers with both amino groups and hydroxyl groups can be used to generate polyurea/polyurethane materials. Furthermore, polyisocyanates with both urea and urethane functionalities can be used to generate polyurea/polyurethane materials.

According to an embodiment the shell is polyurea-based made from, for example but not limited to isocyanate-based monomers and amine-containing crosslinkers such as guanidine carbonate and/or guanazole. Preferred polyurea-based microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to another embodiment, the shell is polyurethane-based made from, for example but not limited to polyisocyanate and polyols, polyamide, polyester, etc.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazole (all percentages being defined by weight relative to the total weight of the colloidal stabilizer). According to another embodiment, the emulsifier is an anionic or amphiphilic biopolymer preferably chosen from the group consisting of polyacrylate (and copolymers especially with acrylamide), gum acacia, soy protein, pectin, gelatin, sodium caseinate and mixtures thereof.

According to a particular embodiment, the polyisocyanate is an aromatic polyisocyanate, preferably comprising a phenyl, a toluyl, a xylyl, a naphthyl or a diphenyl moiety. Preferred aromatic polyisocyanates are biurets and polyisocyanurates, more preferably a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N).

According to a particular embodiment, the polyisocyanate is a trimethylol propane-adduct of xylylene diisocyanate (commercially available from Mitsui Chemicals under the tradename Takenate® D-110N).

Examples of processes for the preparation of polyurea- and polyureathane-based microcapsule slurry are for instance described in WO2007/004166, EP 2300146, EP2579976 the contents of which is also included by reference. Typically a process for the preparation of polyurea- or polyurethane-based microcapsule slurry include the following steps:
 a) dissolving at least one polyisocyanate having at least two isocyanate groups in an oil to form an oil phase;
 b) preparing an aqueous solution of an emulsifier or colloidal stabilizer to form a water phase;
 c) adding the oil phase to the water phase to form an oil-in-water dispersion, wherein the mean droplet size is comprised between 1 and 500 µm, preferably between 5 and 50 µm;
 d) applying conditions sufficient to induce interfacial polymerisation and form microcapsules in form of a slurry.

According to an embodiment, the shell of the microcapsule is based on melamine formaldehyde resin or melamine formaldehyde resin cross-linked with at least one polyisocyanate or aromatic polyols.

According to an embodiment, the shell comprises an aminoplast copolymer, such as melamine-formaldehyde or urea-formaldehyde or cross-linked melamine formaldehyde or melamine glyoxal.

According to a particular embodiment, the core-shell microcapsules are cross-linked melamine formaldehyde microcapsules obtainable by a process comprising the steps of:
1) admixing a perfume oil with at least a polyisocyanate having at least two isocyanate functional groups to form an oil phase;
2) dispersing or dissolving into water an aminoplast resin and optionally a stabilizer to form a water phase;
3) adding the oil phase to the water phase to form an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain a dried core-shell microcapsule;

This process is described in more details in WO 2013/092375 and WO 2015/110568, the contents of which are included by reference.

According to a particular embodiment, the core-shell microcapsule is a formaldehyde-free capsule. A typical process for the preparation of aminoplast formaldehyde-free microcapsules slurry comprises the steps of:
 1) preparing an oligomeric composition comprising the reaction product of, or obtainable by reacting together a) a polyamine component in the form of melamine or of a mixture of melamine and at least one $C_1$-$C_4$ compound comprising two $NH_2$ functional groups;
b) an aldehyde component in the form of a mixture of glyoxal, a $C_{4-6}$ 2,2-dialkoxy-ethanal and optionally a glyoxalate, said mixture having a molar ratio glyoxal/ $C_{4-6}$ 2,2-dialkoxy-ethanal comprised between 1/1 and 10/1; and
c) a protic acid catalyst;
2) preparing an oil-in-water dispersion, wherein the droplet size is comprised between 1 and 600 um, and comprising:
  i. an oil;
  ii. a water medium
  iii. at least an oligomeric composition as obtained in step 1;
  iv. at least a cross-linker selected amongst
    A) $C_4$-$C_{12}$ aromatic or aliphatic di- or tri-isocyanates and their biurets, triurets, trimmers, trimethylol propane-adduct and mixtures thereof; and/or
    B) a di- or tri-oxiran compounds of formula A-(oxiran-2-ylmethyl)$_n$
      wherein n stands for 2 or 3 and 1 represents a $C_2$-$C_6$ group optionally comprising from 2 to 6 nitrogen and/or oxygen atoms;
  v. optionally a $C_1$-$C_4$ compounds comprising two $NH_2$ functional groups;
3) heating said dispersion;
4) cooling said dispersion.

This process is described in more details in WO 2013/068255, the content of which is included by reference.

According to an embodiment, prior to step (ii), microcapsules are rinsed to remove the excess of emulsifier. Microcapsules can be rinsed for example by centrifugation and resuspended in water after withdrawing the supernatant.

Step (ii) and Step (iii)—Mineralization and Crystal Growth

Without being bound by theory, it is believed that the charged terminating surface is providing functional anchoring sites and a high local density of charge groups and nucleation sites onto the surface of the microcapsules resulting in improved adsorption of mineral precursor species followed by initiation of the crystal growth process through in-situ addition of a precipitating species.

Mineral precursors are adsorbed to the surface of microcapsules by incubating the charged capsules in at least one solution containing oppositely charged mineral precursor, providing sufficient agitation and time to allow for complete coverage of capsule surfaces. Removal of excess precursor from solution to prevent generation of free crystalline material in solution can be done and is followed by initiation of the crystal growth process through in-situ addition of a precipitating species.

The person skilled in the art will be able to select suitable conditions for the crystal growth process (for example, precursor selection, reaction conditions, the solution concentrations, incubation times, agitation speeds, temperatures and pH conditions).

Typically:
mineralization occurs at room temperature,
incubation of precursor takes place from 24-72 hours,
the nature of the precipitation species depends on the nature of the precursor.

According to a particular embodiment, the mineral precursor solution is chosen in the group consisting of an iron (II) sulfate solution (comprising iron ions as precursor), an iron (III) chloride solution (comprising iron ions as precursor), calcium-based salt solution (comprising calcium ions as precursor), phosphate-based salt solution (comprising phosphate ions as precursor), carbonate-based salt solution (comprising carbonate ions as precursor), titanium-based precursor solution, zinc-based precursor solution, and mixtures thereof.

One may cite for example titanium alkoxides as titanium-based precursor or zinc alkoxides, zinc acetate, zinc chloride as zinc-based precursor solution.

According to a particular embodiment, the mineral precursor solution is chosen in the group consisting of an iron (II) sulfate solution (comprising iron ions as precursor), an iron (III) chloride solution (comprising iron ions as precursor), calcium-based salt solution (comprising calcium ions as precursor), phosphate-based salt solution (comprising phosphate ions as precursor) and mixtures thereof.

The water-soluble calcium-based salt can be chosen in the group consisting of calcium chloride ($CaCl_2$), calcium nitrate ($Ca(NO_3)_2$), calcium bromide ($CaBr_2$), calcium iodide ($CaI_2$), calcium chromate ($CaCrO_4$), calcium acetate ($CaCH_3CO_2$) and mixtures thereof. Most preferred are calcium chloride and calcium nitrate.

The water-soluble phosphate-based salt can be chosen in the group consisting of sodium phosphate (monobasic) ($NaH_2PO_4$), sodium phosphate (dibasic) ($Na_2HPO_4$), sodium phosphate (tribasic): $Na_3PO_4$, Potassium phosphate (monobasic): $KH_2PO_4$, Potassium phosphate (dibasic) ($K_2HPO_4$), potassium phosphate (tribasic) ($K_3PO_4$), ammonium phosphate (monobasic) (($NH_4)H_2PO_4$), ammonium phosphate(dibasic) (($NH_4)_2HPO_4$), ammonium phosphate (tribasic) (($NH_4)_3PO_4$) and mixtures thereof.

The water-soluble carbonate-based salt can be chosen in the group consisting of sodium, potassium and ammonium based carbonates.

It should be understood that the charge of the mineral precursor used in step (ii) of the process is driven by the charge of the terminating surface of the microcapsules.

Embodiment 1

According to an embodiment, the mineral precursor solution is chosen in the group consisting of an iron (II) sulfate solution, or an iron (III) chloride solution.

As said previously, the initiation of the crystal growth process can be done through in-situ addition of a precipitating species. According to this embodiment, when the mineral precursor is an iron solution, irons ions are adsorbed on the anionic surface and precipitating species used is a base for hydrolysis to form an iron oxide layer (for example by addition of a sodium hydroxide solution).

Embodiment 2

According to another embodiment, the mineral precursor solution is a calcium-based salt (comprising calcium ions as precursor). According to this embodiment, calcium ions are adsorbed on the anionic surface. Precipating species in that case is the addition of another salt, preferably a phosphate-based salt (for one hour for example).

Thus, according to this particular embodiment, microcapsules are introduced sequentially in at least two solutions comprising respectively at least one precursor. Preferably, the first solution comprises water-soluble calcium-based salt including a calcium precursor and the second solution comprises water-soluble phosphate-based salt including a phosphate precursor. Addition order could change according to the selection and charge of the underlying terminating layer.

According to a particular embodiment, the first solution comprises calcium nitrate ($Ca(NO_3)_2$) and the second solution comprises sodium phosphate (dibasic) ($Na_2HPO_4$).

Embodiment 3

Still according to another embodiment, when the terminating surface of the microcapsules are cationic, the microcapsules are firstly incubating in carbonate-based salt solution or in a phosphate-based salt solution to adsorb carbonate ions $CO_3^{2-}$ or phosphate ions $PO_4^{3-}$ respectively on the cationic surface followed by an incubation in a calcium-based mineral solution.

According to a particular embodiment, the process for the preparation of the microcapsule slurry comprises the following steps:
  a) dissolving at least one a polyisocyanate having at least two isocyanate groups in an oil comprising a hydrophobic active ingredient to form an oil phase;
  b) preparing an aqueous solution of a charged emulsifier to form a water phase, wherein the charged emulsifier is an anionic emulsifier or a cationic emulsifier;
  c) adding the oil phase to the water phase to form an oil-in-water dispersion;
  d) applying conditions suitable to induce interfacial polymerization to form core/shell microcapsules in the form of a slurry, wherein:
    the shell has an anionic surface when the emulsifier used in step b) is an anionic emulsifier; or
    the shell has a cationic surface when the emulsifier used in step b) is a cationic emulsifier;
  e) coating at least one anionic polyelectrolyte layer on the cationic surface when the emulsifier is a cationic emulsifier to form an anionic surface;
  f) Optionally, dilution or removal of excess emulsifier;
  g) adsorption of a mineral precursor on the anionic surface;
  h) applying conditions suitable to induce crystal growth of the mineral on the anionic surface; and
  i) optionally drying the slurry.

According to this embodiment, the process comprises the preparation of an oil phase by dissolving a polyisocyanate having at least two isocyanate groups in an oil comprising a hydrophobic active ingredient as defined above.

According to a preferred embodiment of the invention, there is used an amount of between 10 and 60%, more preferably between 20 and 50% of oil in the process of the invention, these percentages being defined by weight relative to the total weight of the obtained microcapsule slurry.

Suitable polyisocyanates used according to the invention include aromatic polyisocyanate, aliphatic polyisocyanate and mixtures thereof. Said polyisocyanate comprises at least 2, preferably at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

The at least one polyisocyanate used in the process according to the invention is present in amounts representing from 1 to 15%, preferably from 2 to 8% and more preferably from 2 to 6% by weight of the microcapsule slurry.

The at least one polyisocyanate is dissolved in an oil, which in a particular embodiment contains a perfume or flavour. The oil can contain a further oil-soluble benefit agent to be co-encapsulated with the perfume and flavour with the purpose of delivering additional benefit on top of perfuming or taste-related. As non-limiting examples, ingredients such as cosmetic, skin caring, malodor counteracting, bactericide, fungicide, pharmaceutical or agrochemical ingredient, a diagnostic agent and/or an insect repellent or attractant and mixtures thereof can be used.

According to an embodiment, the process of the present invention includes the use of an anionic or amphiphilic biopolymer in the preparation of the aqueous phase. Those materials defined above include in particular proteins and polysaccharides. The biopolymer is preferably comprised in an amount ranging from 0.1 to 5.0% by weight of the microcapsule slurry, preferably between 0.5 and 2 wt % of the microcapsule slurry.

The above ranges also apply when the process includes the use of a charged emulsifier.

According to a first embodiment, the charged emulsifier used in step b) is an anionic emulsifier and forms an anionic surface when step d) is completed.

According to an embodiment, the anionic emulsifier is selected from the group consisting of polyvinyl alcohol, polyvinyl pyrilidone, gum acacia, casein, sodium caseinate, soy protein, pea protein, milk protein, whey protein, pectin, sericin, bovine serum albumin, gelatin, and mixtures thereof.

According to a particular embodiment, the anionic emulsifier is gum acacia.

According to a second embodiment, a cationic emulsifier is used in step b) and forms a cationic surface when step d) is completed.

As non-limiting examples of cationic emulsifiers, one may cite for example cationically modified polyvinyl alcohol (as an example, cationic C-506 by Kuraray) or chitosan.

According to this embodiment, the process further comprises a step consisting in coating an anionic polyelectrolyte layer to impart a negatively charged surface necessary to induce the crystal growth of the mineral.

To enhance the adsorption of mineral precursors to the terminating anionic functional surface, said surface can be modified through the adsorption of a polyelectrolyte multi-layered scaffolding.

Thus, according to an embodiment, the process comprises a further step after step d) or after step e), consisting in coating at least one cationic polyelectrolyte layer and at least one anionic polyelectrolyte layer, the terminating layer being an anionic polyelectrolyte layer to form the terminating anionic functional surface.

According to this embodiment, the cationic polyelectrolyte layer is disposed on the anionic surface and the anionic polyelectrolyte layer is the last layer to form the terminating anionic functional surface on which the mineral precursor is adsorbed.

Oppositely-charge polyelectrolytes may be sequentially coated onto microcapsules using layer-by-layer polyelectrolyte deposition in order to provide a multi-layered polyelectrolyte scaffold for adsorption of mineral precursors.

According to the invention, the number of layers of the polyelectrolyte scaffolding is not particularly limited.

According to a particular embodiment, the polyelectrolyte scaffolding consists of two pairs of oppositely charged polyelectrolytes layers.

It means that according to this embodiment, after step d) or step e), the process comprises:
  applying a cationic polyelectrolyte layer C1 on the anionic layer;
  applying an anionic polyelectrolyte layer A1 on the cationic polyelectrolyte layer C1,
  applying a cationic polyelectrolyte layer C2 on the anionic polyelectrolyte layer A1;
  applying an anionic polyelectrolyte layer A2 on the cationic polyelectrolyte layer C2, thereby forming the anionic terminating functional surface on which the mineral precursor is adsorbed.

According to an embodiment, the cationic polyelectrolyte layer is chosen in the group consisting of poly(allylamine hydrochloride), poly-L-lysine and chitosan.

According to another embodiment, the anionic polyelectrolyte layer is chosen in the group consisting of poly (sodium 4 styrene sulfonate) (PSS), polyacrylic acid, polyethylene imine, humic acid, carrageenan, gum acacia, and mixtures thereof.

According to a particular embodiment, the anionic polyelectrolyte layer is PSS.

According to a particular embodiment, the process comprises after step h) a further step consisting of hydrolysis of the mineral layer. This can be done for example by addition of sodium hydroxide.

According to a particular embodiment of the invention, the microcapsule slurry can be submitted to a drying, like lyophilisation or spray-drying, to provide the microcapsules as such, i.e. in a powder form. It is understood that any standard method known by a person skilled in the art to perform such drying is applicable. In particular the slurry may be spray-dried preferably in the presence of a polymeric carrier material such as polyvinyl acetate, polyvinyl alcohol, dextrins, maltodextrin, natural or modified starch, sugars, vegetable gums such as gum acacia, pectins, xanthans, alginates, carrageenans or cellulose derivatives to provide microcapsules in a powder form. Preferably, the carrier is a gum Acacia. According to a particular embodiment, the carrier material contains free perfume oil which can be same or different from the perfume from the core of the microcapsules.

Microcapsule Slurry/Microcapsule Powder

A microcapsule slurry obtainable by the process as defined above is also a subject of the present invention.

Another object of the invention is a microcapsule powder obtained by drying the microcapsule slurry defined above.

Perfuming Composition

Another object of the invention is a perfuming composition comprising
  (i) microcapsules as defined above, wherein the oil-based core comprises a perfume;
  (ii) at least one ingredient selected from the group consisting of a perfumery carrier and a perfuming co-ingredient; and
  (iii) optionally a perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.05 to 30%, preferably between 0.1 and 30% by weight of microcapsules as defined above.

Consumer Product

The invention's microcapsules can advantageously be used in many application fields and used in consumer products. Microcapsules can be used in liquid form applicable to liquid consumer products as well as in powder form, applicable to powdered consumer products.

A consumer product, preferably in the form of a laundry care product, a home care product, a body care product, a skin care product, a hair care product, an air care product, or a hygiene product, comprising microcapsules as defined above, or a perfuming composition as defined above is also an object of the present invention.

Another object of the present invention is a liquid consumer product comprising:
a) from 2 to 65% by weight, relative to the total weight of the consumer product, of at least one surfactant;
b) water or a water-miscible hydrophilic organic solvent; and
c) microcapsule slurry as defined above,
d) optionally non-encapsulated perfume.

A powdered consumer product comprising
(a) from 2 to 65% by weight, relative to the total weight of the consumer product, of at least one surfactant;
(b) microcapsule powder as defined above.
(c) optionally perfume powder that is different from the microcapsules defined above is also an object according to the present invention.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

In particular a liquid consumer product comprising:
a) from 2 to 65% by weight, relative to the total weight of the consumer product, of at least one surfactant;
b) water or a water-miscible hydrophilic organic solvent; and
c) a perfuming composition as defined above is another object of the invention.

Also a powdered consumer product comprising:
(a) from 2 to 65% by weight, relative to the total weight of the consumer product, of at least one surfactant; and
(b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumery consumer product can be a perfume, such as a fine perfume, a cologne or an after-shave lotion; a fabric care product, such as a liquid or solid detergent, tablets and pods, a fabric softener, a dryer sheet, a fabric refresher, an ironing water, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.), a hygiene product such as sanitary napkins, diapers, toilet paper.

According to a particular embodiment, the consumer product is selected from the group consisting of a shampoo, a shower gel, a rinse-off conditioner, a soap bar, a powder or a liquid detergent, a fabric softener and a floor cleaner.

According to a preferred embodiment, the consumer product is a shampoo or a rinse-off conditioner. According to another preferred embodiment, the product is a perfumed soap.

According to another preferred embodiment, the product is a body wash. According to another preferred embodiment, the product is a fabric care product.

Preferably, the consumer product comprises from 0.05 wt %, preferably from 0.1 to 15 wt %, more preferably between 0.2 and 5 wt % of the microcapsules of the present invention, these percentages being defined by weight relative to the total weight of the consumer product. Of course the above concentrations may be adapted according to the olfactive effect desired in each product.

Method for Depositing Microcapsules on a Surface

The mineral layer on microcapsule shell is surprisingly significantly boosting the deposition efficiency and retention of microcapsules on targeted surfaces such as hair and fabric. When microcapsules are applied on a substrate, the percentage of deposition is much higher than that of known delivery systems.

Thus, another object of the invention is a method for depositing microcapsules on a surface, which comprises treating said surface with a perfuming composition as defined above or a consumer product as defined above.

The capsules of the invention have proven to be particularly useful in rinse-off application as their deposition is much superior to delivery systems known heretofore.

The invention will now be further described by way of examples. It will be appreciated that the invention as claimed is not intended to be limited in any way by these examples.

EXAMPLES

Example 1

Preparation of Mineral Coated Polyurea-Based Capsules According to the Invention (A)

Polyurea microcapsules were synthesized according to the formulation described in Table 1, and loaded with a model perfume mixture outlined in Table 2. These microcapsules were then surface-modified with alternating polyelectrolyte multilayers prior to adsorption and hydrolysis of mineral precursors as described in this example.

TABLE 1

Composition of capsules A according to the invention prior to mineralization

| Ingredient | Percentage |
| --- | --- |
| Perfume Oil[1] | 38.0 |
| Uvinul A Plus[2] | 2.0 |
| Trimethylol propane adduct of xylylene diisocyanate[3] | 3.8 |
| Guanidine Carbonate | 0.7 |
| Water for Guanidine Carbonate | 6.3 |
| 2 wt % Anionic Polyvinyl Alcohol Aq. Solution | 49.2 |

[1]Perfuming composition described in Table 2.
[2]Tracer for the quantification of oil deposition
[3]Takenate ® D-110N; origin: Mitsui Chemicals

TABLE 2

Perfume oil composition

| Ingredient | Parts |
| --- | --- |
| Verdox ™[1] | 20.0 |
| Romascone ®[2] | 20.0 |
| Cyclosal | 20.0 |
| Salicynile | 20.0 |
| Acetate de 4-(1,1-dimethylethyl)-1-cyclohexyle[3] | 20.0 |

[1]2-tert-butyl-1-cyclohexyl acetate, Origin: International Flavors & Fragrances, USA
[2]Methyl 2,2-dimethyl-6-methylene-1-cyclohexanecarboxylate, Origin: Firmenich SA, Geneva, Switzerland
[3]Origin: Firmenich SA, Geneva, Switzerland General Protocol for Synthesis of Polyurea Microcapsules:

At least one polyisocyanate (e.g. Trimethylol propane adduct of xylylene diisocyanate Takenate® D-110N) was dissolved in a perfume oil (with Uvinul A Plus tracer). The oil phase was then added to an aqueous emulsifier solution (e.g. 2% polyvinyl alcohol aqueous solution) and homogenized for 4 min using an Ultra-Turrax T25 disperser at 20000 rpm to form an O/W emulsion. The emulsion was pH adjusted to 10 using NaOH solution (counted as the aqueous phase). This emulsion was then stirred at 500 rpm using a mechanical overhead stirrer and optionally a reactant (e.g. a guanidine carbonate solution) was slowly added over 1 hour. Once the addition was complete, the reaction temperature was gradually elevated to 70° C. over 1 h and was maintained at 70° C. for 2 h before being allowed to cool to room temperature.

A core-shell microcapsule slurry is obtained.

General Protocol for Polyelectrolyte Surface Modification:

Incubation of microcapsules in solutions containing a polyelectrolyte with charge opposite to that of the capsule surface results in adsorption of the polyelectrolyte and reversal of the underlying surface charge. Capsules which do not terminate in an anionic polyelectrolyte can be coated using alternating, sequential layer-by-layer deposition of oppositely charged polyelectrolytes. For example, anionic PVOH-stabilized capsules can be coated with cationic polyelectrolyte, polyallylamine hydrochloride (PAH) resulting in a cationic surface. These modified capsules can be again rinsed, and coated with oppositely-charged anionic polystyrene sulfonate (PSS) polyelectrolyte resulting in an anionic surface. The surface layer process, punctuated by rinsing steps can be repeated as many times as required to achieve the desired surface modification.

For this specific surface modification, 10 millilitres of anionic PVOH capsule slurries were incubated in 30 millilitres of a 20 μM solution of PAH (with 10 mM KCl) according to Table 3 for thirty minutes on a rotating plate and subjected to a rinsing procedure of centrifugation at 5000 rpm for 5 minutes followed by removal of the supernatant solution and resuspension in deionized water. This rinsing procedure was repeated three times before initiating the second polyelectrolyte adsorption process by incubation in 30 milliliters of an oppositely charged polyelectrolyte solution of 20 μM PSS (with 10 mM KCl), according to Table 4. The addition of four alternating layers of polyelectrolytes terminated in negatively charged PSS-coated capsule surfaces. The presence of each polyelectrolyte layer was confirmed with zeta potential measurements, and the final PSS layer rendered capsules which were sufficiently negatively-charged. The anionic multi-layered capsules were rinsed prior to mineralization to provide ample scaffolding for directed and selective mineral precursor adsorption on the capsule surfaces.

TABLE 3

Positively charged PAH Solution Composition

| Ingredient | Wt (g) |
| --- | --- |
| Poly(allyamine) HCl (MW = 58000) | 0.174 |
| Potassium Chloride | 0.112 |
| 18.2 MΩ-cm DI water | 150.0 |

TABLE 4

Negatively charged PSS Solution Composition

| Ingredient | Wt (g) |
| --- | --- |
| Poly(sodium 4-styrenesulfonate) (MW = 70000) | 0.210 |
| Potassium Chloride | 0.112 |
| 18.2 MΩ-cm DI water | 150.0 |

General Protocol for Mineralization of Capsules via Incubation and Hydrolysis of Mineral Precursor:

Mineralization of the microcapsule surfaces requires seeding mineral precursor species at the surface of the microcapsules and initiating an in-situ crystal formation reaction. Mineral precursors are adsorbed to the surface of microcapsules by incubating the anionically charged capsules in solutions containing mineral precursor cations, providing sufficient agitation and time to allow for complete coverage of capsule surfaces. Removal of excess precursor from solution to prevent generation of free crystalline material in solution is followed by initiation of the crystal growth process through in-situ addition of a precipitating species.

To make the mineral precursor solution, Iron (II) sulfate crystals were dissolved in deionized water. 10 millilitres of the slurry of anionically charged microcapsules was added to 100 millilitres of the iron (II) sulfate solution and was incubated for 24 hours in a flask while being vigorously stirred by stir bar at 800 rpm. The incubation procedure was punctuated by repeatedly rinsing the capsules. Using centrifugation at 5000 rpm for five minutes to induce phase separation, the remaining iron-laden supernatant was removed and replaced with deionized water. This rinsing procedure was performed three times before inducing hydrolysis of the iron layer on the capsules by dropwise addition of sodium hydroxide until the suspension reached a pH of 9.0, at which point the suspension was incubated on a rotating plate for one hour. After hydrolysis, the suspension was subjected to the rinsing procedure in triplicate by centrifugation at 5000 rpm for five minutes, complete removal of the supernatant, and resuspension in deionized water.

TABLE 5

Mineralization Parameters for Precursor Incubation and Hydrolysis

| Parameter | Mineral Precursor Incubation | Hydrolysis |
| --- | --- | --- |
| Reactant | FeSO$_4$•7H$_2$O | NaOH |
| Concentration | 1.0M | 50 wt % dropwise |
| Volume | 100 mL | 100 mL |
| pH | 3.0 | 9.0 |
| Time (hours) | 24 | 1 |
| Temperature (° C.) | RT (22) | RT (22) |
| Mixing Speed (rpm) | 800 | — |

Example 2

Preparation of Mineral Coated Hybrid Polyurea-Based Capsules According to the Invention (B)

A similar protocol as described in Example 1 was followed to prepare microcapsules with a composition as reported in Table 1. Instead of 4 polyelectrolyte layers, only 2 polyelectrolyte layers (PAH/PSS) were adsorbed to the anionic PVOH capsules, terminating in a negatively charged PSS layer. Mineral precursor incubation and hydrolysis were performed according to protocol described in Example 1.

Example 3

Preparation of Mineral Coated Polyurea-Based Capsules According to the Invention (C)

A similar protocol as described in Example 1 was applied to prepare microcapsules with a composition as reported in Table 6 below. A cationic PVOH emulsifier (Kuraray C506) was used to emulsify the capsules. Only one polyelecrolyte layer of PSS was adsorbed to provide a terminating negative surface charge. Mineral precursor adsorption and hydrolysis were performed according to the protocol described in Example 1.

TABLE 6

Composition of capsules C according to the invention prior to mineralization

| Ingredient | Percentage |
| --- | --- |
| Perfume Oil[1] | 38.0 |
| Uvinul A Plus[2] | 2.0 |
| trimethylol propane adduct of xylylene diisocyanate[3] | 3.8 |
| Guanidine Carbonate | 0.7 |
| Water for Guanidine Carbonate | 6.3 |
| 2 wt % Cationic Polyvinyl Alcohol Aq. Solution | 49.2 |

[1] Perfuming composition described in Table 2.
[2] Tracer for the quantification of oil deposition
[3] Takenate ® D-110N; origin: Mitsui Chemicals Example 4

Preparation of Polyurea-Based Capsules According to the Invention (D)

A similar protocol as described in Example 1 was applied to prepare microcapsules with a composition as reported in Table 1. Polyelectrolyte and mineral precursor adsorption, as well as hydrolysis procedures were the same as described in Example 1. A terminating layer of negatively charged polyelectrolyte (PSS) was adsorbed to the positively charged mineral layer by the same polyelectrolyte adsorption procedure described in Example 1.

Example 5

Preparation of Mineral Coated Polyurea-Based Capsules According to the Invention (E)

A similar protocol as described in Example 1 using a biopolymer emulsifier without additional polyelectrolyte layers was applied to prepare microcapsules with a composition as reported in Table 7 below. A negatively charged biopolymer, gum acacia, was used as the emulsifier to stabilize the microcapsules. No polyelectrolyte addition or rinsing procedures were performed on the microcapsules prior to mineralization of the surface. Mineral precursor adsorption and hydrolysis were performed according to the procedure described in Example 1.

TABLE 7

Composition of capsules D

| Ingredient | Percentage |
| --- | --- |
| Perfume Oil[1] | 38.0 |
| Uvinul A Plus[2] | 2.0 |
| Takenate ® D-110N[3] | 3.8 |
| Guanidine Carbonate | 0.7 |
| Water for Guanidine Carbonate | 6.3 |
| 2 wt % gum acacia emulsifier solution | 49.2 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate

Example 6

Preparation of Mineral Coated Polyurea-Based Capsules According to the Invention (F)

Similar protocol as described in Example 5 was applied to prepare microcapsules with a composition as reported in Table 7. Microcapsules were rinsed three times by centrifugation at 5000 rpm and resuspended in deionized water after withdrawing the supernatant to remove residual gum acacia emulsifier before applying the mineral layer by the procedure described in Example 1.

Example 7

Preparation of Mineral Coated Polyurea-Based Capsules According to the Invention (G)

Similar protocol as described in Example 5 (without addition of sodium hydroxide or guanidine carbonate) was applied to prepare microcapsules with a composition as reported in Table 8. Microcapsules were rinsed three times by centrifugation at 5000 rpm and resuspended in deionized water after withdrawing the supernatant to remove residual gum acacia emulsifier before applying the mineral layer by the procedure described in Example 1.

TABLE 8

Composition of capsules G

| Ingredient | Percentage |
| --- | --- |
| Perfume Oil[1] | 38.0 |
| Uvinul A Plus[2] | 2.0 |
| trimethylol propane adduct of xylylene diisocyanate[3] | 3.8 |
| 2 wt % gum acacia emulsifier solution | 56.2 |

[1]Perfuming composition from Table 9
[2]tracer for the quantification of oil deposition
[3]Takenate ® D-110N; origin: Mitsui Chemicals

TABLE 9

Perfume Oil Composition

| Ingredient | Parts |
| --- | --- |
| Isopropyl Myristate | 0.3 |
| (Z)-3-hexen-1-ol butyrate | 0.6 |
| Delta Damascone | 1.0 |
| 2,4-Dimethyl-3-cyclohexene-1-carbaldehyde | 1.0 |
| Habanolide ®[1] | 3.0 |
| Hedione ®[2] | 5.0 |
| Hexyl Cinnamic Aldehyde | 12.0 |
| Iso E Super ®[3] | 16.0 |
| Verdyl Acetate | 24.0 |
| Lilial ®[4] | 37.0 |

[1]Pentadecenolide, origin: Firmenich SA, Geneva, Switzerland
[2]Methyl-cis-3-oxo-2-pentyl-1-cyclopentane acetate, origin: Firmenich SA, Geneva, Switzerland
[3]7-acetyl, 1,2,3,4,5,6,7,8-octahydro-1,1,6,7-tetramethyl naphthalene, origin International Flavors & Fragrances, USA
[4]3-(4-tert-butylphenyl)-2-methylpropanal, origin Givaudan SA, Vernier, Switzerland

Example 8

Preparation of Mineral Coated Polyurea-Based Capsules According to the Invention (H)

Similar protocol as described in Example 5 (without addition of sodium hydroxide or guanidine carbonate) was applied to prepare microcapsules with a composition as reported in Table 8. Microcapsules were rinsed three times by centrifugation at 5000 rpm and resuspended in deionized water after withdrawing the supernatant to remove residual gum acacia emulsifier before applying the mineral layer by sequential additions of the ionic solutions listed in Table 15. The microcapsule slurry was placed into a dilute buffer solution and subjected to sequential additions of the ionic precursor solutions, starting with the calcium-containing solution, in order to induce precipitation of the calcium based mineral on the surface of the microcapsules. To begin, 45 mL of buffer solution were added to 5 mL of capsule slurry under agitation. Precursor 1 was added over one hour, diluted 1:10 with water, followed by an hour long addition of Precursor 2 solution. This sequence was repeated one to four times at 0.3M concentrations to get a range of surface coverage. The samples were imaged after ageing for 24 hours under agitation.

TABLE 10

Mineralization Parameters for Nucleation and Growth of Calcium Phosphate Based Mineral Layer

| Parameter | Precursor 1 Addition | Precursor 2 Addition |
| --- | --- | --- |
| Reactant | $Ca(NO_3)_2$ | $Na_2HPO_4$ |
| Concentration | 0.3M | 0.18M |
| Volume | 10 mL | 10 mL |
| pH | 8.5 | 8.5 |
| Addition Time (hours) | 1 | 1 |
| Temperature (° C.) | RT (22) | RT (22) |
| Mixing Speed (rpm) | 200 | 200 |

Example 9

Preparation of Polyurea-Based Control Capsules According to the Invention (V, W, X, Y, Z)

A similar protocol as described in Example 1 was applied to prepare control microcapsules with a composition as reported in Table 1 (for Capsules V and W), Table 6 (for Capsule X), Table 7 (for Capsule Y), and Table 8 for Capsule Z. Guanidine carbonate was used as reactant for all control capsules with the exception of Capsule Z. The control capsules are unmodified or have polyelectrolyte layers without mineralization. Capsule V had a negative surface charge from the negative polyvinyl alcohol emulsifier and was prepared without the polyelectrolyte addition, rinsing, or mineralization procedures (Capsule V is the control template for Capsule B). Capsule W was prepared by rinsing and adding four polyelectrolyte layers terminating in a negatively charged PSS layer, according to the procedure described in Example 1, but without the mineralization procedure (Capsule W is the control template for Capsule A and Capsule D). Capsule X was prepared by addition of a single negatively charged PSS polyelectrolyte layer to the cationic capsules, but with no subsequent mineralization (Capsule X is the control template for Capsule C). Capsule Y was prepared without rinsing, polyelectrolyte addition, or mineralization of the gum acacia stabilized capsules (Capsule Y is the control template for Capsule E and Capsule F). Capsule Z was prepared without rinsing, polyelectrolyte addition or mineralization of the gum acacia stabilized capsules (Capsule Z is the control template for Capsule G).

Example 10

Figure 2:
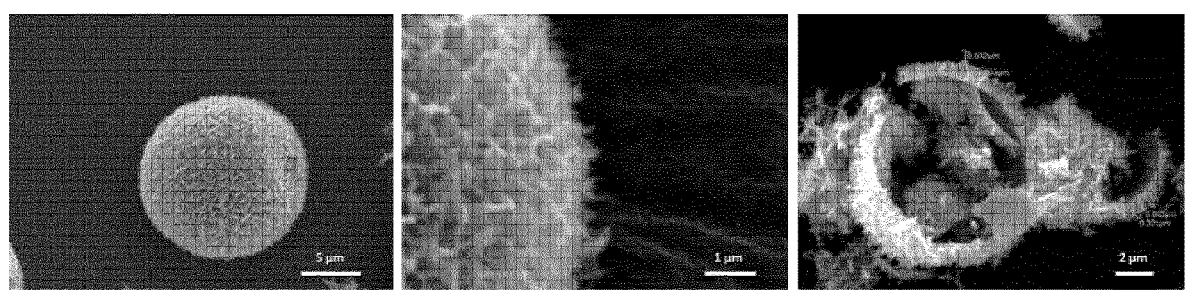
FIG. 2 represents scanning electron micrographs of the mineralized surface of microcapsules according to the invention (Capsules A) achieved through directed growth of the mineral layer (goethite).
Figure 3:
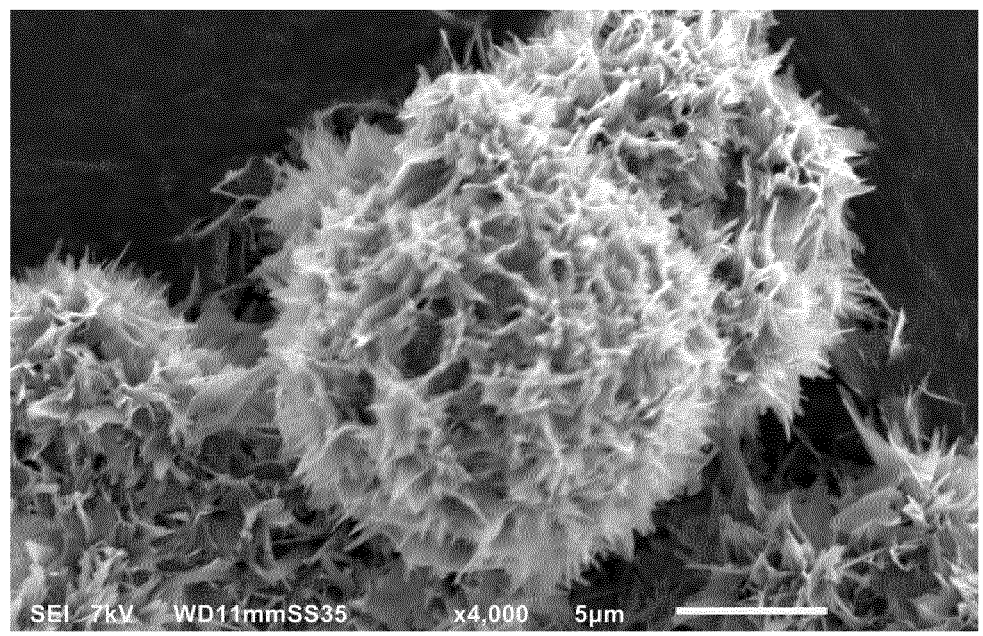
FIG. 3 represents scanning electron micrographs of the mineralized surface of microcapsules according to the invention (Capsules H) achieved through directed growth of the mineral layer (calcium phosphate).

Capsules Characterization and Deposition Results
Microscopy of Capsules:

To image the microcapsules, dilute capsule slurries were dried onto carbon tape, which was adhered to aluminium stubs and then sputter coated with a gold/palladium plasma. The stubs were placed into a scanning electron microscope (JEOL 6010 PLUS LA) for analysis. Images of Capsule A, Capsule B, Capsule C, and Control Capsules X, Y and Z are shown in FIG. 1 to illustrate that stable, robust, rough mineralized microcapsules can be generated by growing spinulose mineral layers onto smooth polyurea microcapsule scaffolds. Surface features and the shell profile are further illustrated in FIG. 2 for Capsules A. Surface features are further illustrated in FIG. 3 for Capsules H.

Deposition Testing on Hair:

For the quantification of deposition, the following procedure was used in triplicate. A 500 mg mini brown Caucasian hair swatch was wet with 40 mL of tap water (39° C.) aimed at the mount with a 140 mL syringe. The excess water was gently squeezed out once and 0.1 mL of a model surfactant mixture containing microcapsules loaded with a UV tracer (Uvinul A Plus) was applied with a 100 μL positive displacement pipet. The surfactant mixture was distributed with 10 horizontal and 10 vertical passes. The swatch was then rinsed with 100 mL of tap water (39° C.) with 50 mL applied to each side of the swatch aimed at the mount. The excess water was gently squeezed out and the hair swatch was then cut into a pre-weighed 20 mL scintillation vial. This process was repeated in triplicate and then the vials containing the cut hair were dried in a vacuum oven at 50-60° C. (100 Torr) for at least 5 hours. After the drying process, the vials were again weighed to determine the mass of the hair in the vials. Controls were also prepared by adding 0.1 mL of a model surfactant mixture containing microcapsules to an empty vial. 4 mL of 200 proof ethanol were then added to each vial and they were subjected to 60 min of sonication. After sonication, the samples were filtered through a 0.45 μm PTFE filter and analysed with a HPLC using a UV detector. To determine the percentage of deposition of microcapsules from a model surfactant mixture, the amount of Uvinul extracted from the hair samples was compared to the amount of Uvinul extracted from the control samples.

TABLE 11

Model Surfactant Mixture

| Ingredient | Actives Percentage |
|---|---|
| Sodium Laurel Ether Sulfate (SLES) | 17.2 |
| Cocamidopropyl Betaine (CAPB) | 10.0 |
| Acrylamidopropyltrimonium chloride/acrylamide copolymer[1] | 0.5 |
| Water | 72.3 |
| Microcapsule Slurry (Equivalent Oil) | 0.5 |
| pH Adjustment (Citric Acid to pH 5.5) | *** |

[1]Salcare ® SC 60; origin BASF

Deposition onto hair swatches was measured from this simplified model surfactant mixture which is meant to be representative of personal cleansing formulations such as shampoo or shower gel. The quantitative deposition values are given in Table 12 and the results are shown in FIG. 4.

Figure 4:
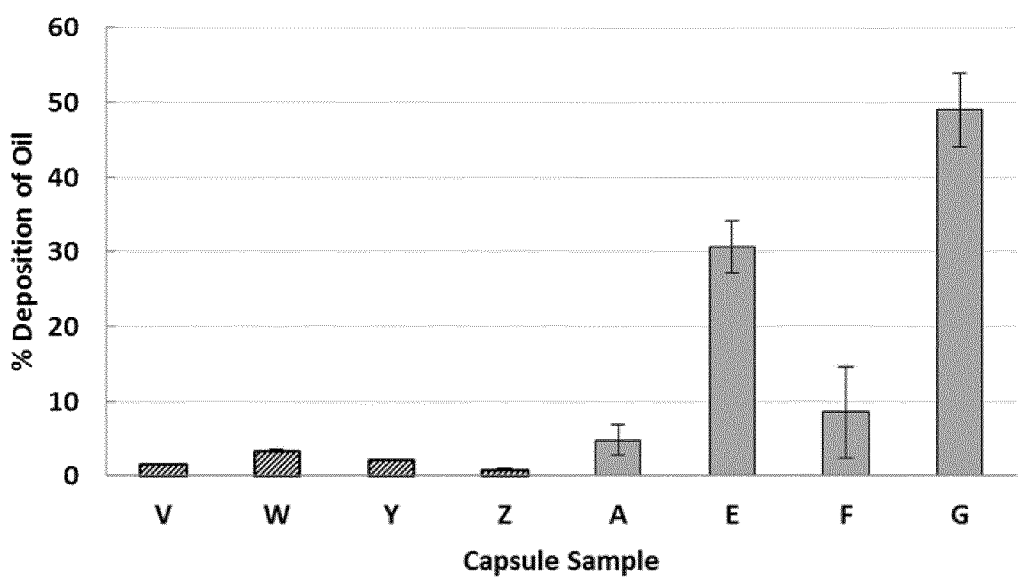
FIG. 4 represents the percentage of microcapsule deposition of mineralized microcapsules according to the invention (Capsules A, E, F, G) compared to smooth relevant control capsules (Capsules V, W, Y, Z) onto hair after rinsing from a model surfactant mixture loaded at 0.5 wt % equivalent free oil.
Figure 5:
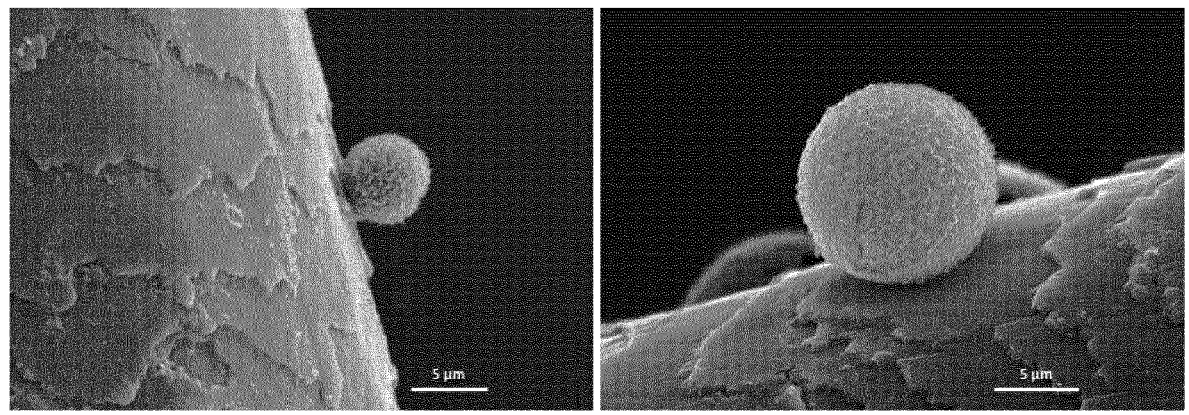
FIG. 5 represents scanning electron micrographs of microcapsules according to the invention (mineralized Capsules A) deposited onto Caucasian, brunette, virgin hair from a model surfactant mixture after rinsing.

The data illustrated in FIG. 4 demonstrate that the addition of a mineral layer to an anionic PVOH-stabilized capsule increases the deposition onto hair swatches significantly from 1.6% for the control capsules W to 4.8% for the mineralized capsules A. The capsules according to the invention are boosting deposition up to 3 times better than prior art capsules. Comparing Capsule E to the relevant, unmineralized gum acacia-stabilized microcapsule control, Capsule Z, the deposition percentage is increased from 2.16% deposition of oil onto hair to 30.71% deposition onto hair. Over one order of magnitude improvement (14× more oil) is achieved through the mineralization of the smooth biopolymer-stabilized capsule surface, and this improvement is tremendous. The specific affinity and improved deposition of the mineralized microcapsules for the targeted biological substrate after rinsing is shown in the micrographs of FIG. 5.

The deposition protocol was used to test the deposition of Capsule H (capsules with a rough calcium phosphate mineral coating) compared to the deposition performance of the smooth control Capsule Y onto hair swatches from the model surfactant system. The mineralized Capsule Y prototype (FIG. 3) was determined to deposit 3.74 times more oil onto hair swatches after rinsing compared to the unmineralized smooth control Capsule Y.

TABLE 12

Deposition of Control Capsules (V, W, Y, Z) and Capsules of the Invention: Capsules (A-G) onto Hair from a Model Surfactant System

| Microcapsules Sample | Percent Deposition |
|---|---|
| V | 1.56 |
| W | 3.39 |
| Y | 2.16 |
| Z | 0.85 |
| A | 4.79 |
| E | 30.71 |
| F | 8.5 |
| G | 49.02 |

Example 11

Deposition Performance in Detergent Base for Fabric Care Applications

Capsules A, B, C, and D according to the inventions described in Examples 1-4 respectively were tested in different formulation bases along with control Capsule W and Capsule X. The capsules were suspended in the model detergent base 24 hours prior to deposition testing performed on fabric in a method analogous to the method described in Example 10 for tracer-loaded microcapsules. Capsules were loaded into the formulations at 0.5 wt % equivalent free oil.

Deposition Protocol for Detergent Applications:

Capsule deposition on fabric from a commercially available, unscented detergent base ("Tide, free & gentle" Procter & Gamble: Water; sodium alcoholethoxy sulfate; propylene glycol; borax; ethanol; linear alkylbenzene sulfonate sodium salt; polyethyleneimine ethoxylate; diethylene glycol; trans sulfated & ethoxylated hexamethylene diamine; alcohol ethoxylate; linear alkylbenzene sulfonate, MEA salt; sodium formate; sodium alkyl sulfate; DTPA; amine oxide; calcium formate; disodium diaminostilbene disulfonate; amylase, protease; dimethicone; benzisothiazolinone) was performed by subjecting fabric swatches to a miniaturized laundry simulator. The detergent base was loaded with capsule slurry at 0.5 wt % equivalent free oil, which was subsequently loaded into tap water at 1% by volume. A 1 gram fabric swatch was submerged into 30 millilitres of the solution in a 50 mL centrifuge tube. The solution containing the fabric swatch was subjected to high speed vortexing for 10 seconds. The fabric swatch was removed and placed into a clean tube, which was filled with fresh tap water and vortexed for another 10 seconds to simulate the rinse cycle. The water was removed from the tube and the process of refilling the tube with fresh tap water and vortexing was repeated an additional two times before removing the fabric swatch and hanging it to air dry on a laundry rack. Once dry, the swatches were subjected to the same extraction and tracer analysis protocol as described for hair deposition in Example 9.

Figure 6:
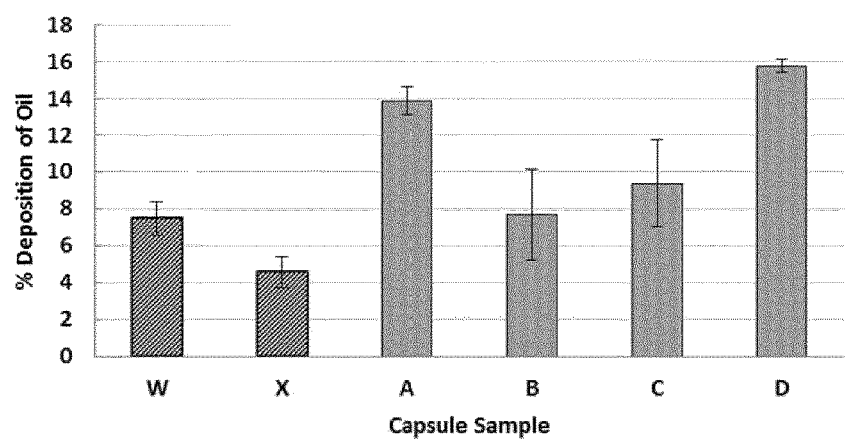
FIG. 6 represents the percentage of microcapsule deposition of mineralized microcapsules according to the invention (Capsules A, B, C and D) compared to smooth control capsules (Capsules W and X) onto a 1 g cotton fabric swatch from a model detergent base after subjecting swatch to a miniaturized laundry cycle simulation.

Quantitative deposition results are shown in Table 13 and are shown graphically in FIG. 6. Capsules according to the invention deposit very well onto fabric swatches after rinsing off complex formulations such as detergent, and tend to deposit twice the amount of oil compared to the smooth template control capsules. Capsule D deposits twice the mass of oil onto the fabric swatches compared to the relevant control Capsule W. Capsule C deposits twice the oil payload deposited by control Capsule X.

TABLE 13

Quantitative deposition results on 1 gram towel fabric swatches after rinsing for Capsules A, B, C, and D and Control Capsules W, X from a commercial, unscented laundry detergent formulation using the detergent deposition protocol.

| Microcapsules Sample | Percent Deposition onto 1 g Fabric Swatch from Detergent After Rinsing |
|---|---|
| W | 7.5 |
| X | 4.6 |
| A | 13.9 |
| B | 7.7 |
| C | 9.4 |
| D | 15.8 |

Example 12

Deposition Performance in Fabric Softener Base for Fabric Application

Capsules A, B, C, and D according to the inventions described in Examples 1-4 respectively were tested in a model fabric softener base ("Downy Ultra, free & gentle" by Procter & Gamble: Water; Diethyl ester dimethyl ammonium chloride; Calcium Chloride; Formic acid; Hydrochloric acid; Polydimethylsiloxane; Methylisothiazolinone/Methylchloroisothiazolinone; Cationic polymer; Diethylenetriamine pentaacetate, sodium salt) along with Capsules W and Capsules X (controls). The capsules were suspended in the model, commercially available fabric softener base 24 hours prior to deposition testing performed as described in Example 9. Capsules were loaded into the fabric softener base at 0.2 wt % equivalent free oil.

Figure 7:
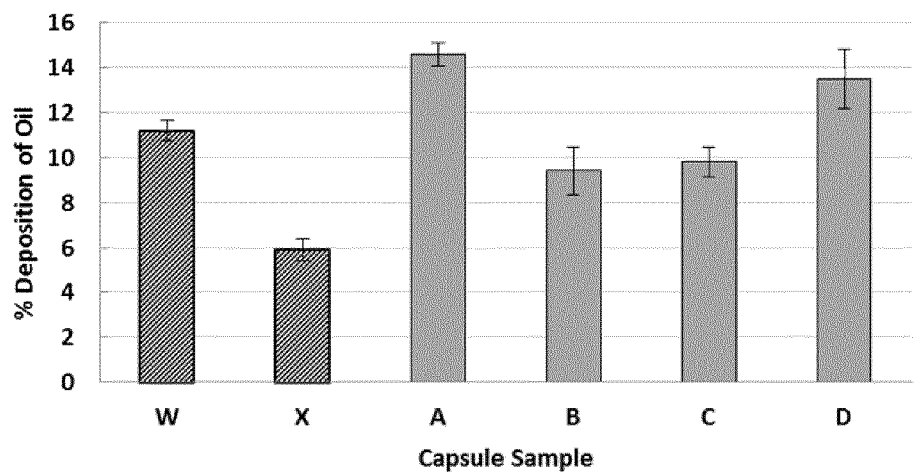
FIG. 7 represents the percentage of microcapsule deposition of mineralized capsules according to the invention (Capsules A, B, C and D) compared to smooth control capsules (Capsules W and X) onto a 1 g cotton fabric swatch from a model fabric softener base after subjecting swatch to a miniaturized laundry cycle simulation.

Deposition Protocol for Fabric Softener Applications:

Quantitative capsule deposition on fabric from a fabric softener application was assessed using a similar protocol to that described in Example 11 for the deposition of capsules from a model detergent base. The fabric softener was loaded with capsule slurry at 0.2 wt % equivalent free oil, which was subsequently loaded into tap water at 1% by volume. The quantitative deposition results are shown in Table 14. FIG. 7 illustrates that mineralized capsules deposited more oil onto fabric after rinsing compared to the most relevant smooth capsule controls (i.e. Capsules A compared to Capsules W; Capsules C compared to Capsules X) and all mineralized capsules showed high deposition efficiency after rinsing.

TABLE 14

Quantitative deposition results on 1 gram towel fabric swatches after rinsing for Capsules A, B, C, and D and Control Capsules W, X from a commercial, fabric softener formulation using the fabric softener deposition protocol.

| Microcapsules Sample | Percent Deposition on 1 g Fabric Swatch from Fabric Softener After Rinsing |
|---|---|
| W | 11.2 |
| X | 5.9 |
| A | 14.6 |
| B | 9.4 |
| C | 9.8 |
| D | 13.5 |

Example 13

Bulk Depletion of Capsules by Fabric Swatch During Washing

Figure 8:
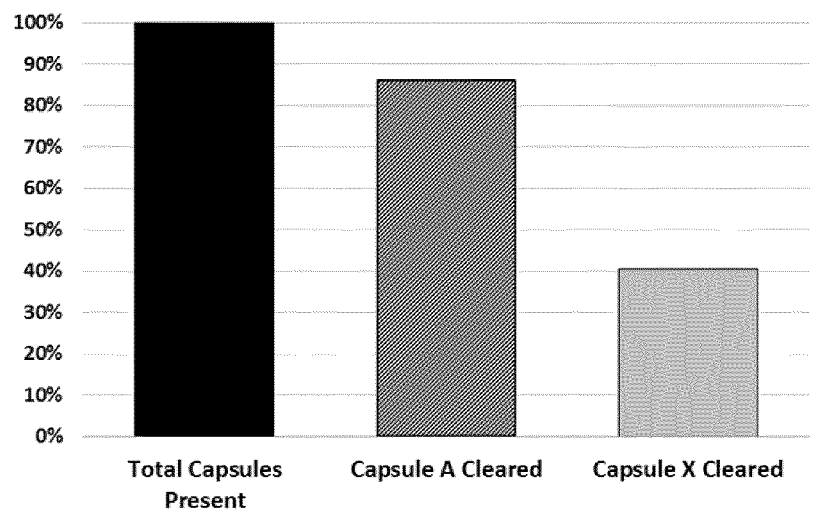
FIG. 8 represents the percentage of bulk capsule concentration cleared by a 1 g fabric swatch after high speed vortexing in a solution loaded with a diluted softener solution containing 0.2 wt % encapsulated oil.

The depletion of capsules from a bulk washing solution by a 1 g cotton fabric swatch during the miniature laundry cycle described in Example 11 and Example 12 was quantitatively assessed using the same extraction and tracer analysis protocol described in Example 9. The bulk solution comprised 30 mL of tap water and 1% by volume fabric softener solution containing capsule slurry (loaded at 0.2 wt % equivalent free oil) of either Capsule A or Capsule W. The initial solution bulk capsule concentration was determined prior to the immersion of a 1 g towel fabric swatch. To initiate the miniaturized laundry cycle, a 1 g fabric swatch was added to this bulk solution in a 50 mL centrifuge tube and subjected to 10 seconds of vortexing on a high speed vortexer. The fabric swatch remained in the centrifuge, and the bulk capsule concentration was determined by pulling an aliquot of solution. The fabric swatch attracts and removes bound capsules from solution, depleting the bulk concentration. The remaining bulk solution was analyzed for tracer content once again to determine the depletion efficiency of the fabric swatches as a function of capsule type in bulk solution. The percentage of the original capsule content cleared by a fabric swatch for both Capsule A and a control Capsule W are shown in FIG. 8. Using this depletion test method, the fabric swatch clears more than 85% of mineralized Capsules A from the starting bulk concentration (100%). In contrast, the same mass and dimension of fabric only removes 40% of control Capsules W from the bulk concentration.

Example 14

Evaluating Sensory Performance of Mineralized Microcapsules on Hair

Figure 9:
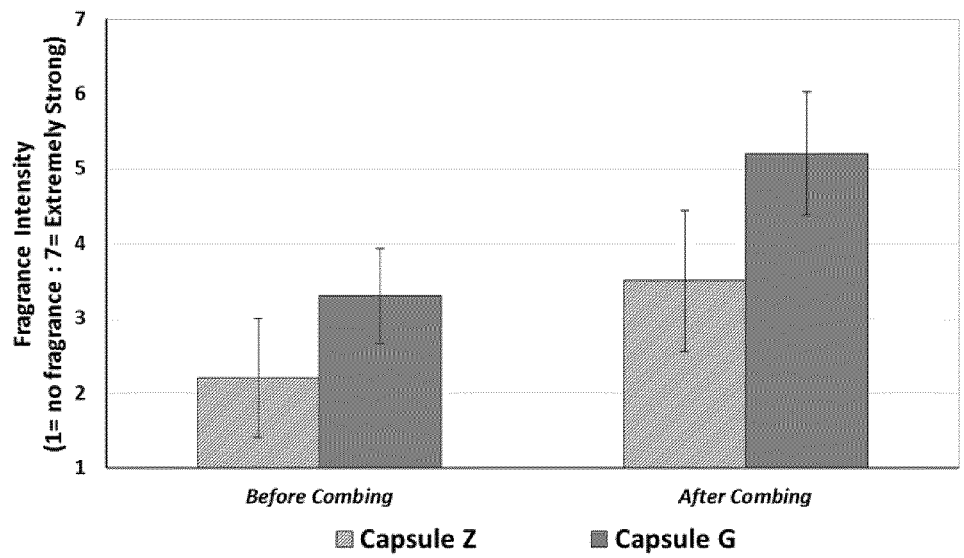
FIG. 9 represents the olfactive evaluation of microcapsules deposited onto hair from a model surfactant mixture before and after combing (capsule Z—not part of the invention and capsule G—according to the invention).

Capsules G and Capsules Z were each separately placed into model surfactant mixture (Table 11) at 0.5 wt % equivalent oil and applied to hair swatches by the same procedure described in Example 10, rinsed, and allowed to dry on a rack for 24 hours. Hair swatches were then evaluated for olfactive intensity, combed, then reevaluated. Olfactive intensities were rated on a scale from 1-7, 1 indicating no fragrance intensity and 7 indicating extremely strong fragrance intensity. The results for olfactive intensity are shown in Table 15, and in FIG. 9. Mineralized Capsule G provided much stronger olfactive intensity after combing than did smooth control Capsule Z.

TABLE 15

Olfactive evaluation of microcapsules deposited onto hair from a model surfactant mixture (0.5% fragrance oil) before and after combing. Olfactive intensity was rated from 1-7. Mineralized Capsule G had greater initial fragrance intensity and greater fragrance intensity after combing compared to the relevant smooth control Capsule Z as evaluated by n = 10 panelists.

| Microcapsule Sample | Time of Evaluation | Fragrance Intensity |
| --- | --- | --- |
| Capsule Z | Before Combing | 2.2 |
|  | After Combing | 3.5 |
| Capsule G | Before Combing | 3.3 |
|  | After Combing | 5.2 |

Example 15

Figure 10:
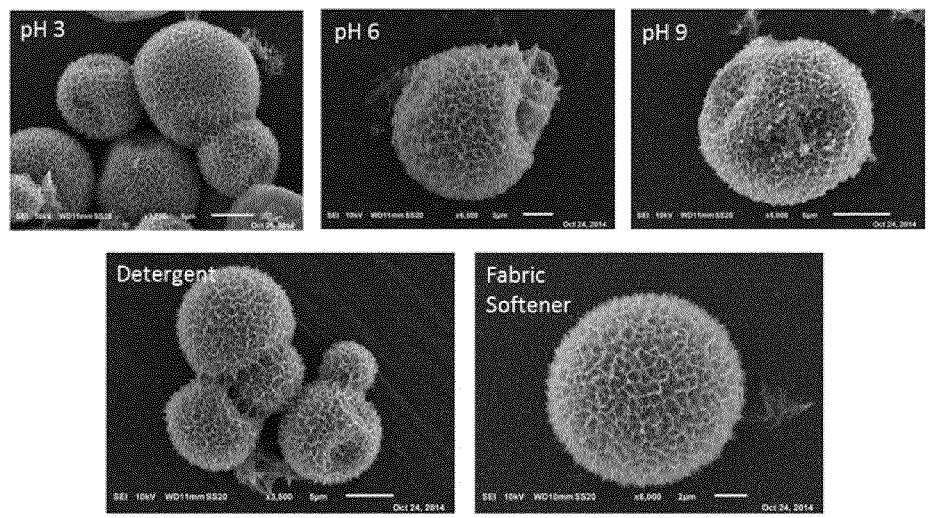
FIG. 10 represents scanning electron micrographs showing stability of mineralized microcapsules subjected to various pH conditions and different surfactant systems after a period of 4 weeks.

Stability of Robust Mineralized Surface Features Following Incubation in Various Solutions To test the robustness of the mineral layers, samples of Capsule A microcapsules were incubated in different solution with varying pH values (pH adjusted deionized water at pH 3, pH 6 and pH 9), as well as in different application formulations (laundry detergent and fabric softener). As shown in the micrographs of FIG. 10, the surface features were maintained following incubation in the various harsh solution conditions after 4 weeks. This is an indication of the robustness of the surface architecture of the mineral layer, which does not dissolve or undergo appreciable structural changes.

Example 16

Figure 11:
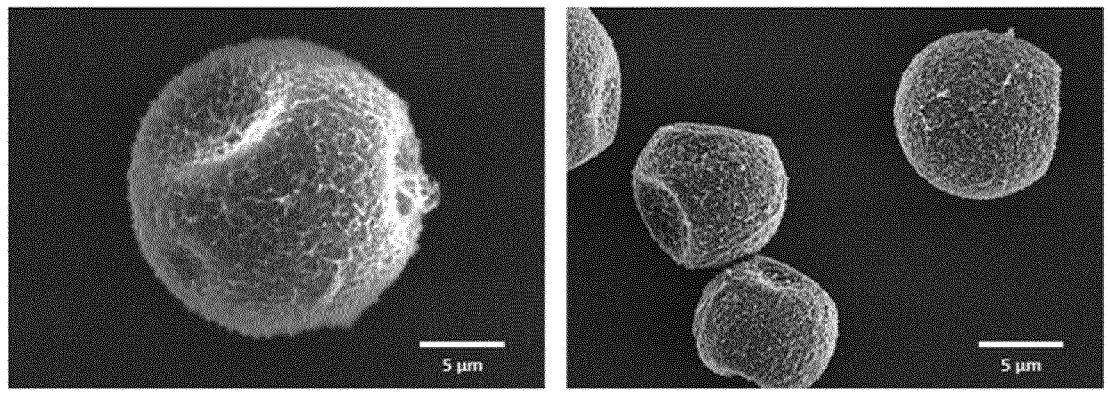
FIG. 11 represents scanning electron micrographs showing mineralized microcapsule stability after being subjected to drying by lyophilization.

Generation of Dried Mineralized Capsule Powder with Maintained Surface Roughness A sample of Capsules E from Example 5 were synthesized and dried to produce varied powder formulations using a Labconco Freezone 6 lyophilization unit. The capsule slurries containing 5-40% oil were dried by freezing the slurries to the internal walls of round-bottom flasks by rotating the slurry-filled flasks in dry ice and then affixing the flask to a lyophilization tower and increasing the vacuum to remove the frozen water phase by sublimation. Images of the freeze-dried powders are given in FIG. 11. The capsules survived lyophilisation, and the layer was robust enough to withstand the freeze-drying processing conditions without losing surface roughness or encapsulated oil.

Example 17

Surface Roughness Characterization
Microcapsule Surface Roughness Characterization Characterization of microcapsule surfaces was conducted using a Keyence VK laser scanning confocal microscope profilometer to quantify the surface roughness of different microcapsules. The profile of each capsule was surveyed using a violet range confocal laser and the resulting surface profiles were analyzed by Keyence software to calculate the key roughness parameters of each profile, including average roughness ($R_a$), mean roughness depth ($R_z$) and additionally, root mean square roughness ($R_q$). Curvature of surveyed capsules was accounted for using a filter to flatten the characterized area for measurement purposes. Measurements of vertical profiles were determined along scan lines. An Atomic Force Microscope (Dimension Icon AFM with a ScanAsyst-Air cantilever by Bruker) was also used in Peak-Force tapping topographical mode to evaluate surface features and roughness parameters (processed using Bruker NanoScope Analysis software) to correlate different surface roughness parameters such as maximum roughness ($R_t$) with deposition.

Significant differences in nanoscale roughness between smooth capsules and the textured, rough, mineralized capsules in this invention were established. Using both analytical methods, there is a clear correlation between increased values for different roughness parameters and enhanced deposition as shown in FIG. 15.

Figure 12:
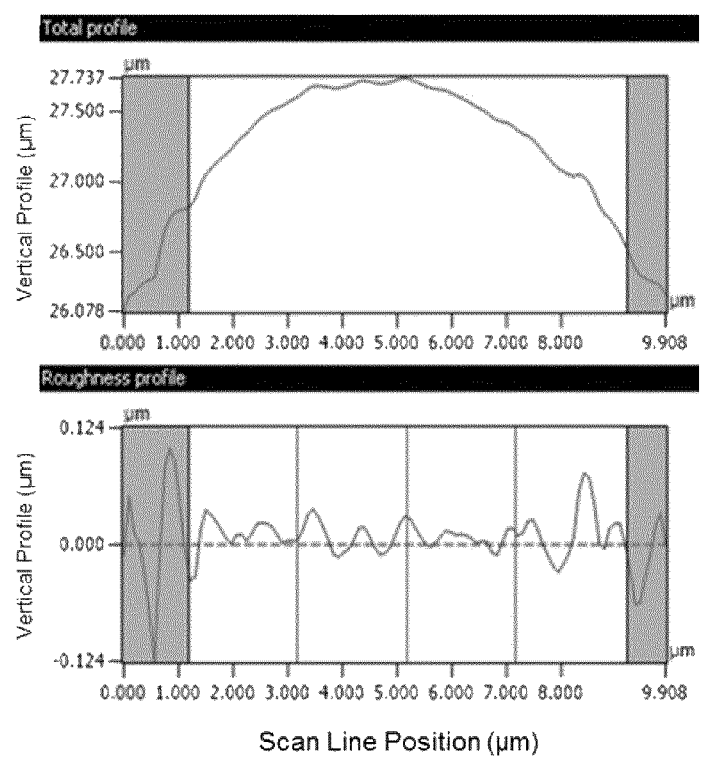
FIG. 12 depicts measured total and curvature-corrected surface roughness profiles (y axis) as a function of analyzed segment scan length (x axis) obtained using a Keyence VK laser scanning confocal microscope for Capsule V smooth control.
Figure 13:
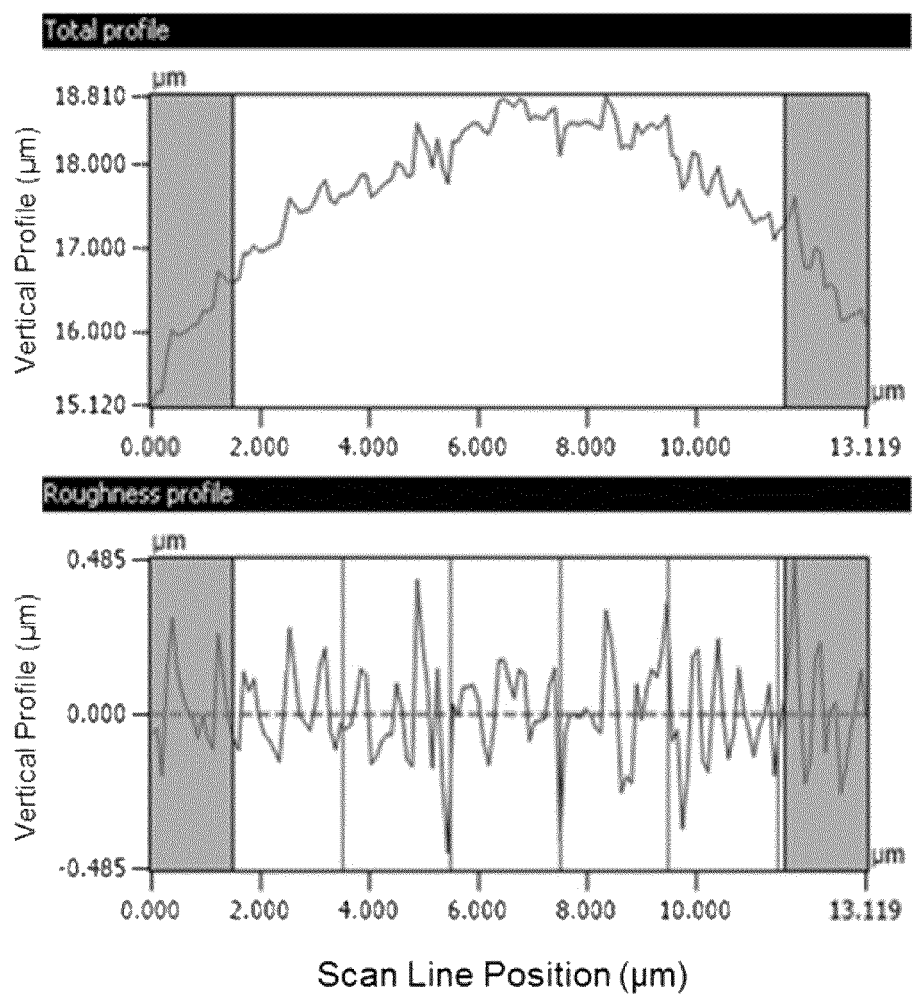
FIG. 13 depicts measured total and curvature-corrected surface roughness profiles (y axis) as a function of analyzed segment scan length (x axis) obtained using Keyence VK laser scanning confocal microscope for Capsule F rough mineralized capsule.

According to FIGS. 12 and 13, where the vertical profile is shown as a function of scan line position, one can conclude from the Keyence VK measurements that there are apparent differences in the topographies of smooth and rough mineralized capsules. The curved surface of the control Capsule V (FIG. 12) has minimal roughness on the micro scale as compared to the vertical profile of the rough mineralized capsule (Capsule F, FIG. 13) which has significantly pronounced surface features with increased frequency and peak heights, confirming the presence of rough surface features visualized by scanning electron microscopy.

Figure 14:
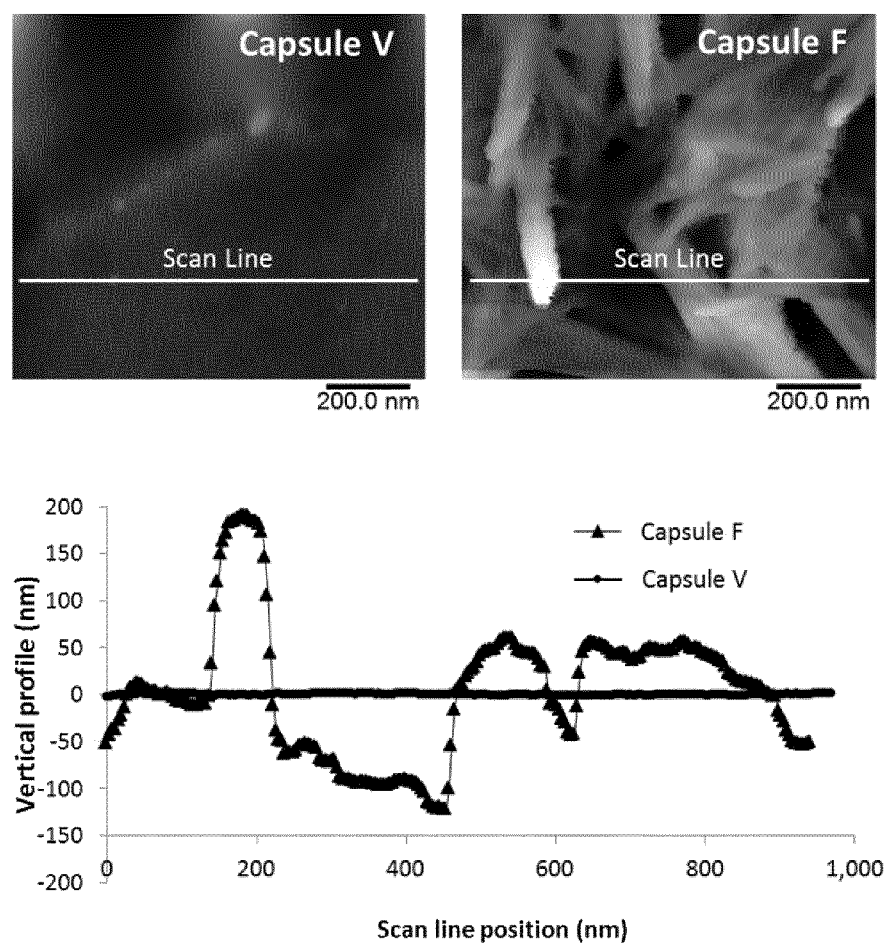
FIG. 14 depicts measured roughness profiles for smooth (V) and rough (F) capsules analyzed using a Dimension ICON Atomic Force Microscope from Bruker along the 1 micron scan lines indicated.

According to FIG. 14, one can conclude from the AFM measurements that there are obvious differences in the vertical roughness profiles of a smooth capsule (control Capsule V) compared to a rough mineralized capsule (Capsule F) along the 1 micron scan line indicated for the corresponding AFM images. The topography of the rough mineralized Capsule F with a spinulose coating contains pronounced features with large peak to valley differences in contrast to the relatively flat vertical profile for smooth Capsule V along the same scan length.

Figure 15:
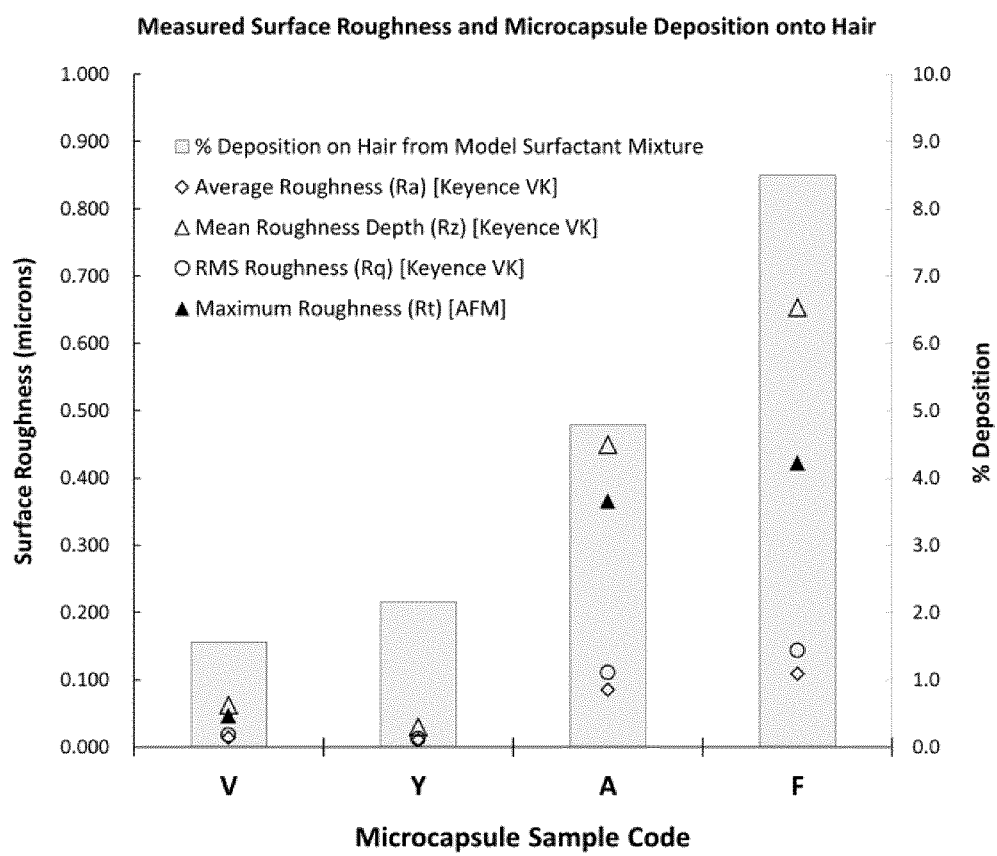
FIG. 15 depicts measured roughness parameters determined using two instruments (Keyence VK confocal laser scanning microscope profilometer and Dimension ICON atomic force microscope) plotted against capsule deposition performance onto hair from a model surfactant mixture after rinsing for rough (A, F) and smooth control capsules (V, Y). Using both characterization techniques, increased surface roughness strongly correlates with increased deposition of capsules onto hair after rinsing.

According to FIG. 15, there is strong correlation between increased microcapsule deposition and greater surface roughness as determined by two different instruments and profilometric techniques and captured by various relevant roughness parameters $R_a$, $R_z$, $R_q$, $R_t$. Significantly enhanced deposition of rough, textured mineralized Capsules A and F onto hair from a rinse-off model surfactant mixture is related to significantly higher $R_a$, $R_z$, $R_q$, and $R_t$ values compared to the relevant smooth control Capsules V and Y respectively. The preservation of the trends and correlation with enhanced deposition are clearly shown for all roughness parameters and are especially apparent for the mean roughness depth $R_z$ values determined using the Keyence VK and maximum roughness $R_t$ determined using the Bruker AFM.

The invention claimed is:

1. A mineralized core-shell microcapsule slurry comprising at least one microcapsule having:
   a) an oil-based core comprising a hydrophobic active ingredient;
   b) a polymeric shell having a terminating charged functional surface; and
   c) a mineral layer on the terminating charged functional surface, wherein the mineral layer has a roughness profile having at least one of an arithmetical mean roughness value ($R_a$) greater than 50 nm and/or a mean roughness depth ($R_z$) greater than 100 nm.

2. The mineralized core-shell microcapsule slurry according to claim 1, wherein the mineral layer does not comprise silicon oxides.

3. The mineralized core-shell microcapsule slurry according to claim 1, wherein the mineral layer comprises a material chosen from the group consisting of iron oxides, iron oxyhydroxide, titanium oxides, zinc oxides, calcium carbonates, calcium phosphates and mixtures thereof.

4. The mineralized core-shell microcapsule slurry according to claim 1, wherein the terminating charged functional surface is an anionic surface and wherein the at least one microcapsule comprises a polyelectrolyte scaffolding between the anionic surface and the mineral layer, said polyelectrolyte scaffolding including at least one cationic polyelectrolyte layer and at least one anionic polyelectrolyte layer with the proviso that the terminating layer is an anionic polyelectrolyte layer.

5. The mineralized core-shell microcapsule slurry according to claim 1, wherein the polymeric shell is made of a material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/gum acacia shell wall and mixtures thereof.

6. The mineralized core-shell microcapsule slurry according to claim 1, wherein the oil-based core comprises a perfume oil.

7. A consumer product comprising microcapsules as defined in claim 1.

8. The consumer product of claim 7 in a form of a fine fragrance product, laundry care product, a home care product, a body care product, a hair care product, a skin care product, an air care product, or a hygiene product.

9. The mineralized core-shell microcapsule slurry according to claim 1, wherein the oil-based core is a perfume.

10. A perfuming composition comprising
  (i) perfume microcapsules as defined in claim 6;
  (ii) at least one ingredient selected from the group consisting of a perfumery carrier and a perfuming co-ingredient; and
  (iii) optionally a perfumery adjuvant.

11. A consumer product comprising the perfuming composition as defined in claim 10.

12. The consumer product of claim 11 in a form of a fine fragrance product, laundry care product, a home care product, a body care product, a hair care product, a skin care product, an air care product, or a hygiene product.

13. A process for preparing the mineralized core-shell microcapsule slurry as defined in claim 1 comprising the steps of:
  (i) Preparing a core-shell microcapsule slurry comprising microcapsules having a terminating charged functional surface;
  (ii) Adsorbing at least one mineral precursor on the terminating charged functional surface; and
  (iii) Applying conditions suitable to induce crystal growth of the at least one mineral precursor on the terminating charged functional surface to form a mineral layer.

14. The process according to claim 13, wherein the core-shell microcapsule slurry in step (i) is formed by interfacial polymerization in the presence of a charged emulsifier.

15. The process according to claim 14, wherein the charged emulsifier is an anionic emulsifier and forms a terminating anionic functional surface when the interfacial polymerization is completed in step (i).

16. The process according to claim 14, wherein the charged emulsifier is a cationic emulsifier that forms a terminating cationic functional surface when the interfacial polymerization is completed, and wherein step (i) further comprises a step of coating at least one anionic polyelectrolyte layer on the terminating cationic functional surface to form a core-shell microcapsule having a terminating anionic functional surface.

17. The process according to claim 13, wherein the at least one mineral precursor is adsorbed on a terminating anionic functional surface by incubating the core-shell microcapsule slurry obtained in step (i) in at least one mineral precursor solution, wherein the at least one mineral precursor solution is chosen from the group consisting of iron (II) sulfate solution, iron (III) chloride solution, calcium-based salt solution, phosphate-based salt solution, carbonate based salt solution, titanium-based precursor solution, zinc-based precursor solution, and mixtures thereof.

18. The process according to claim 13, wherein the at least one mineral precursor does not comprise silicon oxides.

* * * * *